United States Patent
Izu et al.

(10) Patent No.: US 6,194,190 B1
(45) Date of Patent: Feb. 27, 2001

(54) AMINO-TERMINAL DEBLOCKING ENZYME

(75) Inventors: Yukiko Izu, Kusatsu; Tetsuki Tanaka, Moriyama; Masaru Miyagi, Kusatsu; Tetsuo Tanigawa, Otsu; Jun Tomono, Muko; Susumu Tsunasawa, Otsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/202,832

(22) PCT Filed: Jun. 19, 1997

(86) PCT No.: PCT/JP97/02121

§ 371 Date: Dec. 21, 1998

§ 102(e) Date: Dec. 21, 1998

(87) PCT Pub. No.: WO97/49819

PCT Pub. Date: Dec. 31, 1997

(30) Foreign Application Priority Data

Jun. 24, 1996 (JP) .................................... 8-184050

(51) Int. Cl.[7] .............................. C12N 9/50; C12N 9/48; C12N 15/63; C12Q 1/44
(52) U.S. Cl. ......................... 435/227; 435/24; 435/69.1; 435/183; 435/219; 435/212; 435/320.1; 435/252.3; 435/68.1; 435/19; 536/23.2; 536/23.3; 536/23.7; 530/350
(58) Field of Search ......................... 435/227, 24, 320.1, 435/69.1, 183, 252.3, 219, 212; 536/23.2, 23.7, 24.3; 530/350

(56) References Cited

FOREIGN PATENT DOCUMENTS 6-319566 * 11/1994 (JP) .
7-298881   11/1995 (JP) .

OTHER PUBLICATIONS

Takara Shuzo Ltd. Thermostable Aminopeptidase gene, Genback Accession No: Q75345, Aug. 30, 1995.*

* cited by examiner

*Primary Examiner*—Rebecca E. Prouty
*Assistant Examiner*—Richard Hutson
(74) *Attorney, Agent, or Firm*—Birch, Stewart, Kolasch & Birch, LLP

(57) ABSTRACT

To provide an amino terminal protecting group-releasing enzyme characterized in that the enzyme possesses an activity for releasing a protecting group by acting on a peptide of which amino terminal is blocked by the protecting group, and exhibits the activity for two or more protecting groups, or a functional equivalent thereof; a DNA encoding the same; a method for producing the enzyme; a method for removing amino terminal protecting group including the step of subjecting to a reaction with the enzyme to release amino terminal protecting group; and a method for analyzing an amino acid sequence. The above enzyme is useful in the analysis of an amino acid sequence of peptides, particularly proteins and peptides, of which amino terminal is blocked by unknown protecting groups.

19 Claims, 12 Drawing Sheets

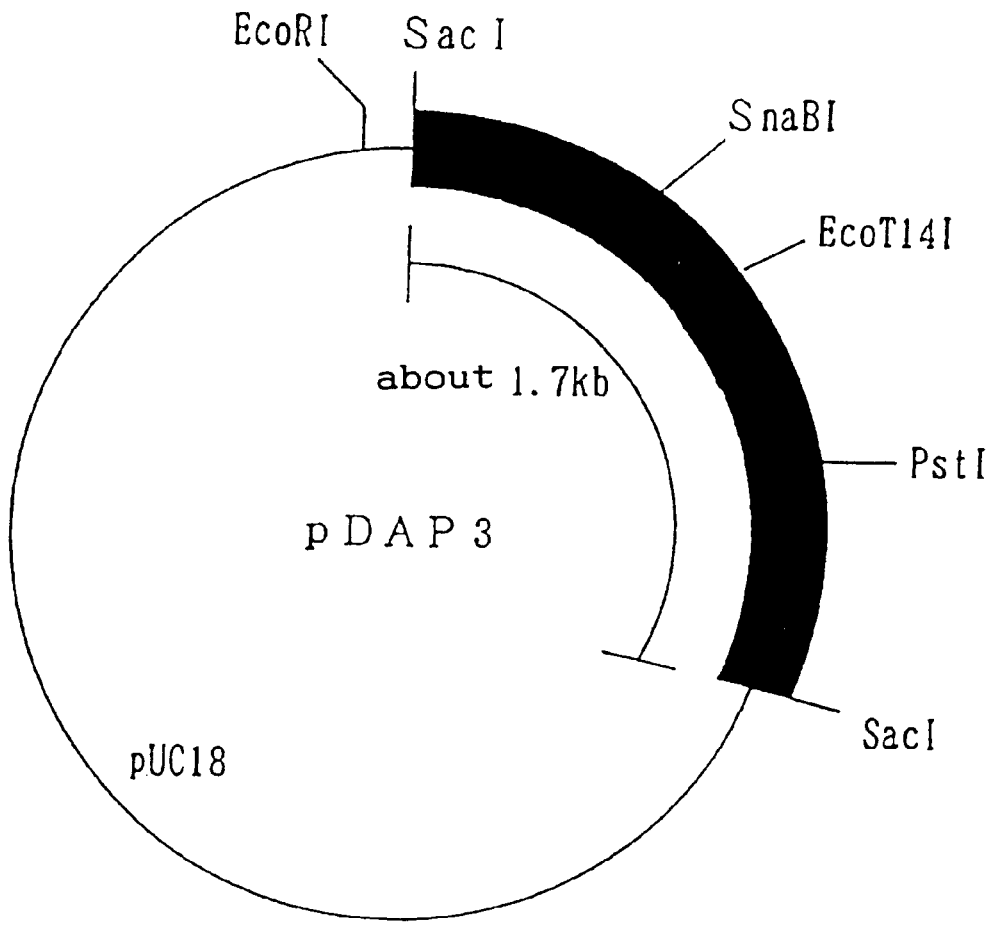
F I G. 1

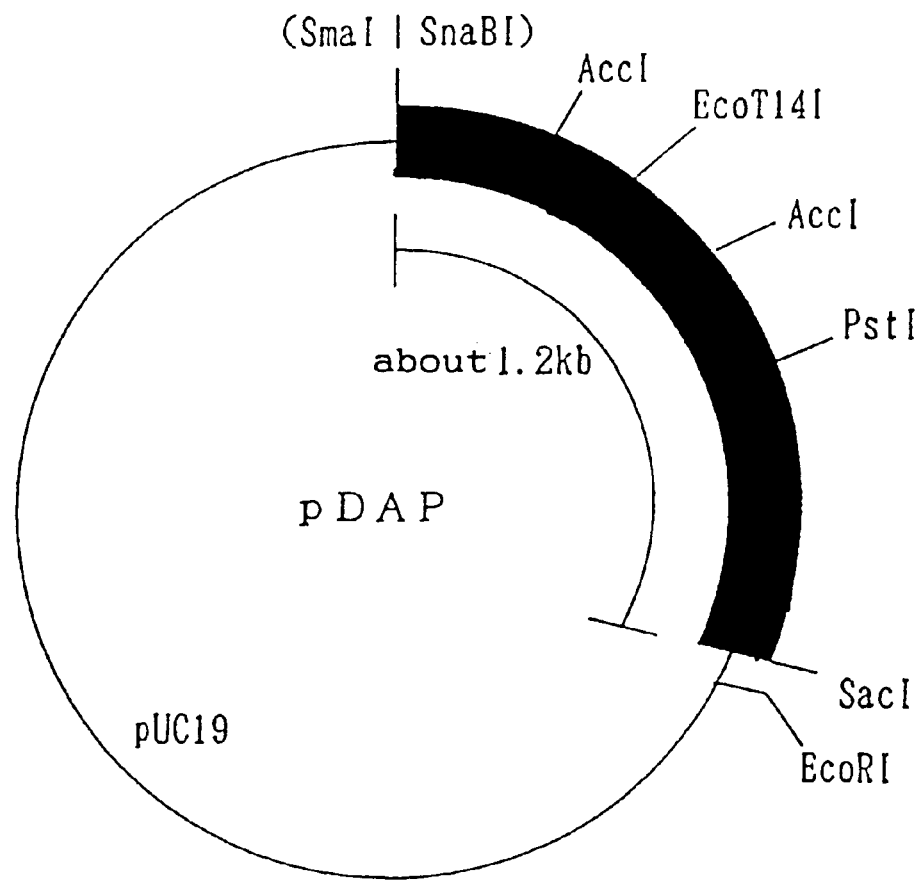
F I G. 2

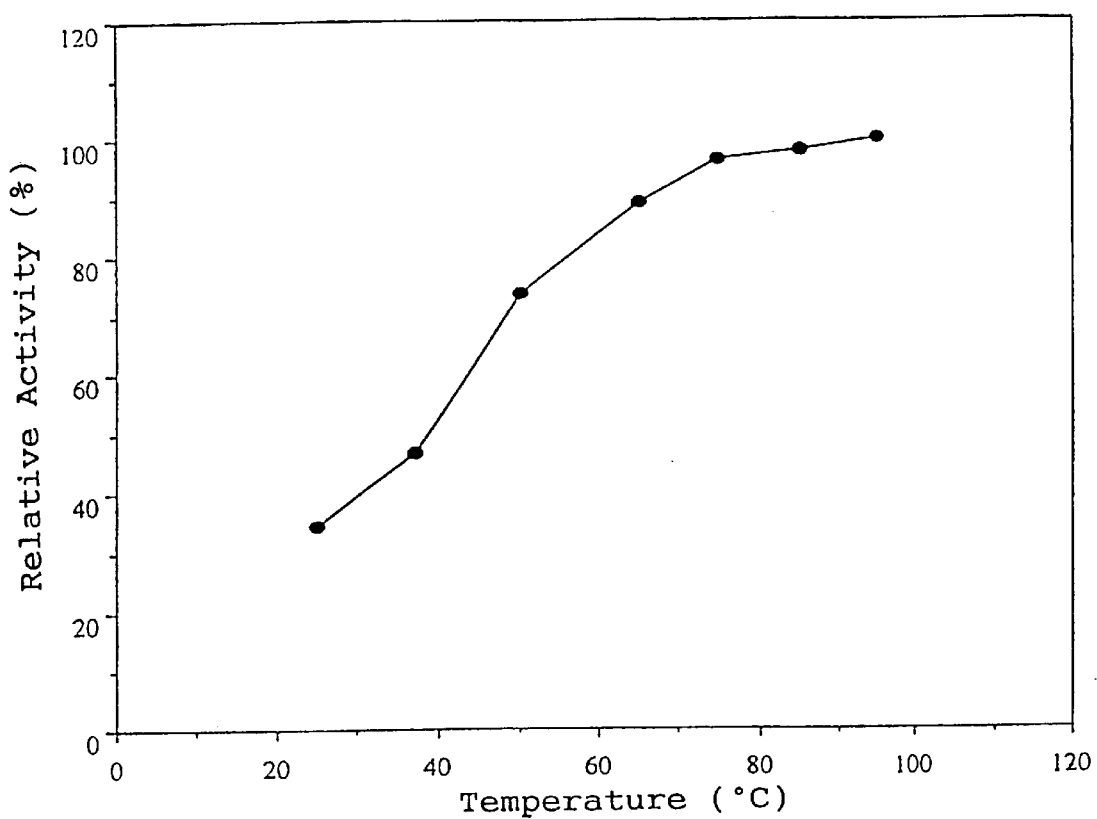
F I G. 3

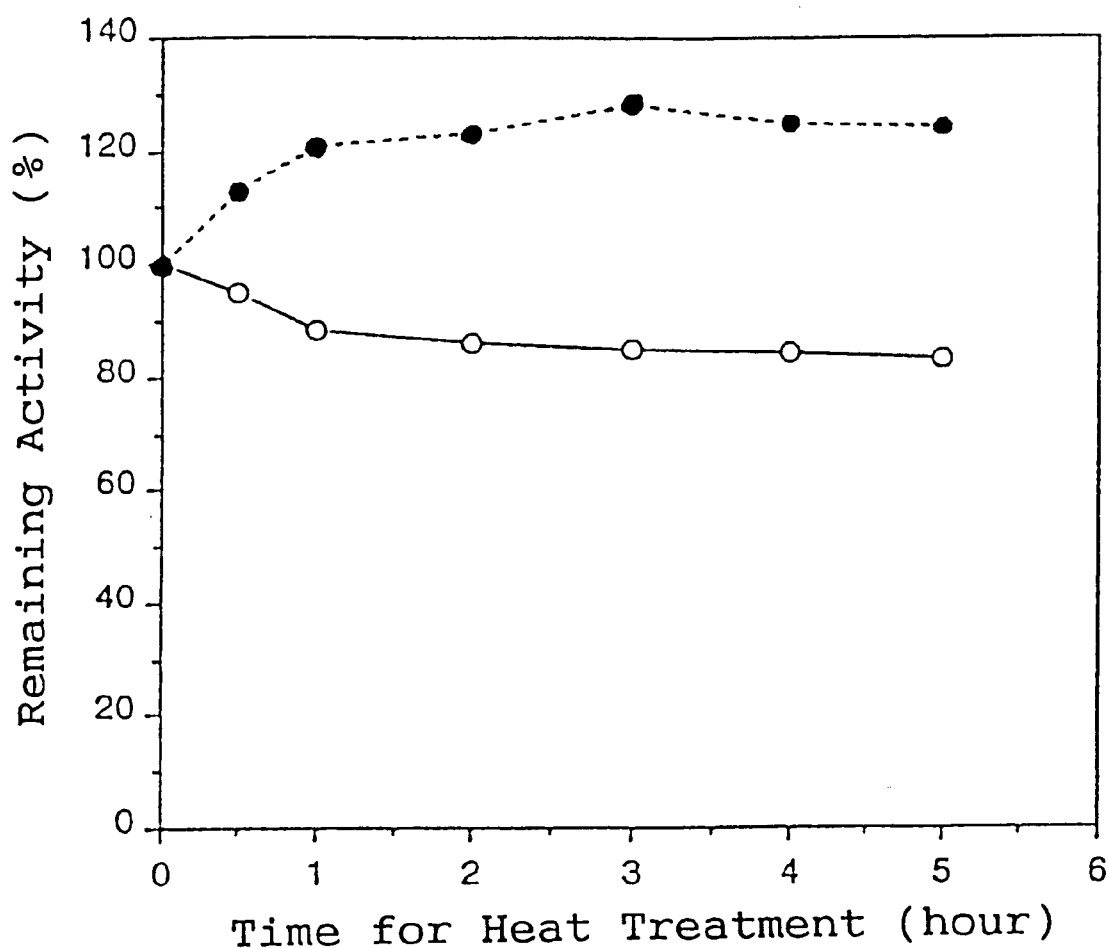
F I G. 5

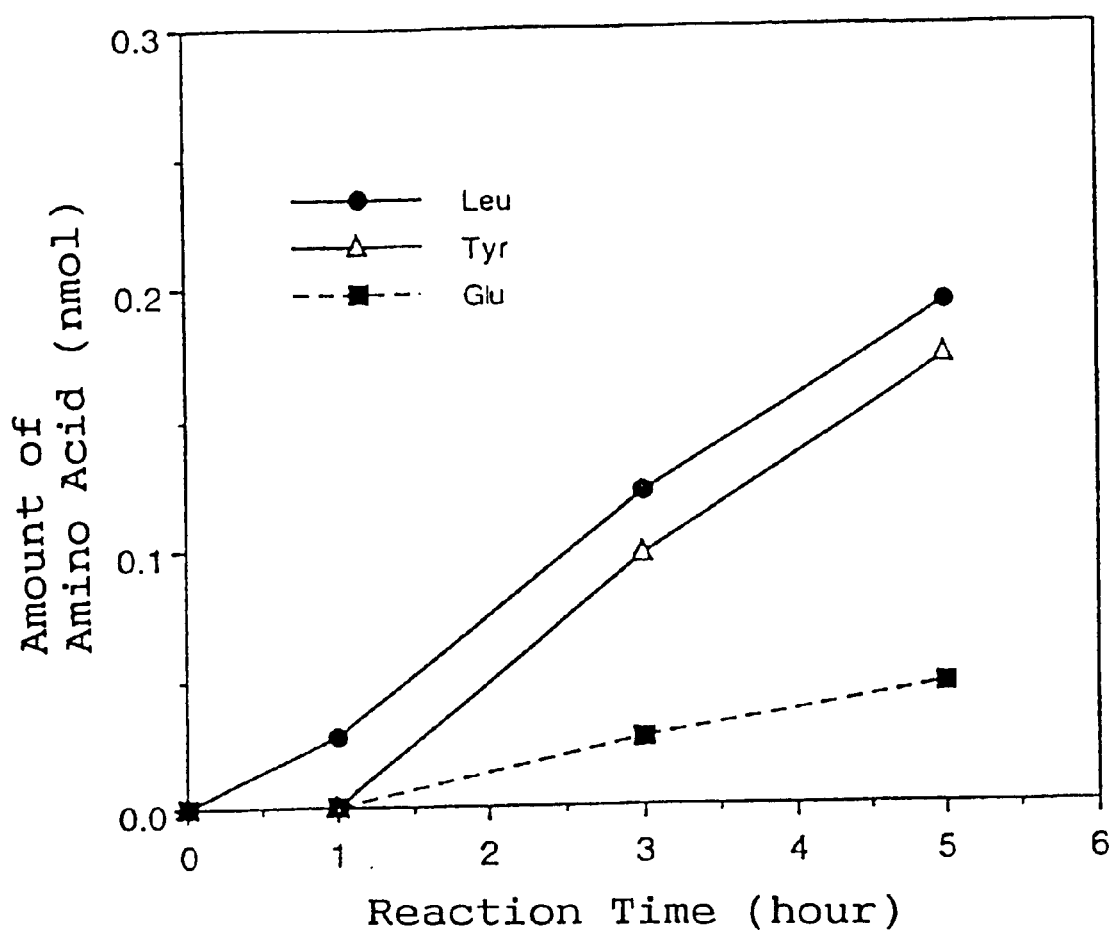
F I G. 6

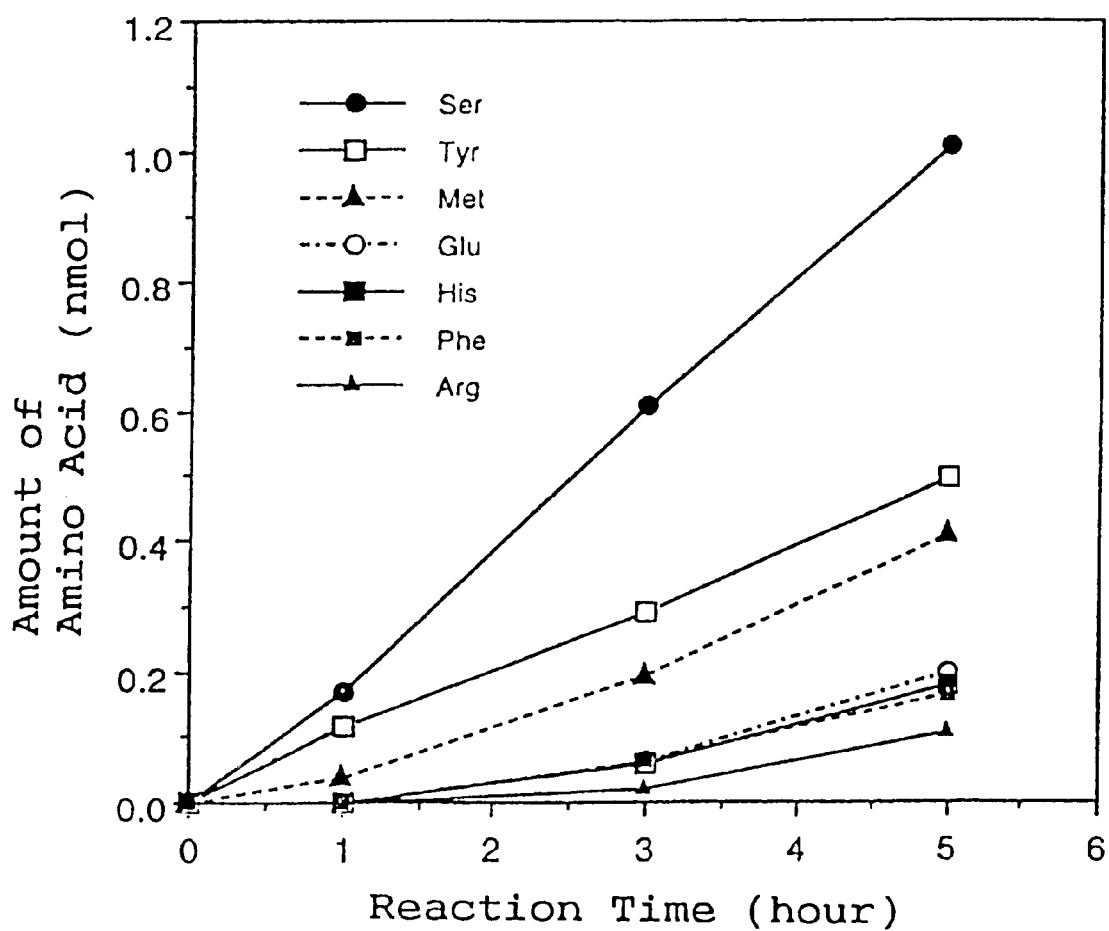
F I G. 7

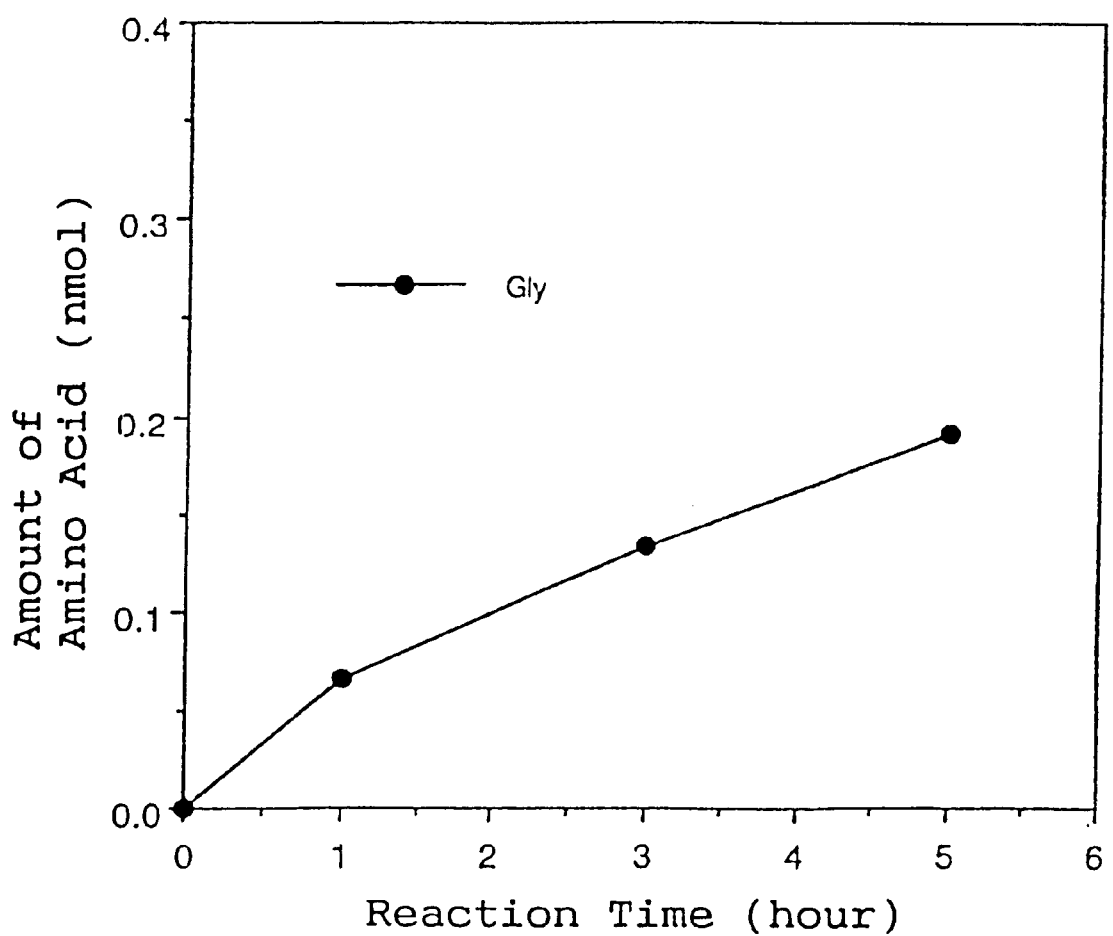
F I G. 8

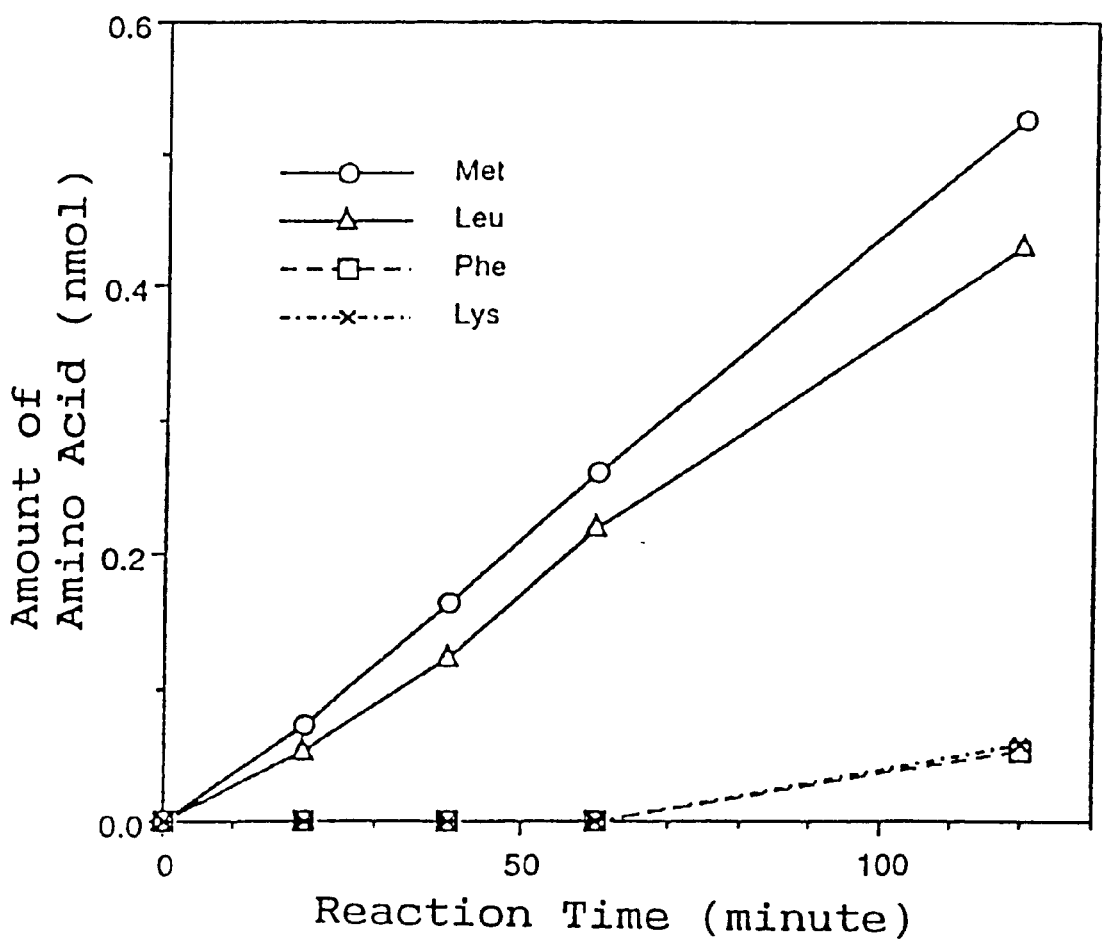
F I G. 9

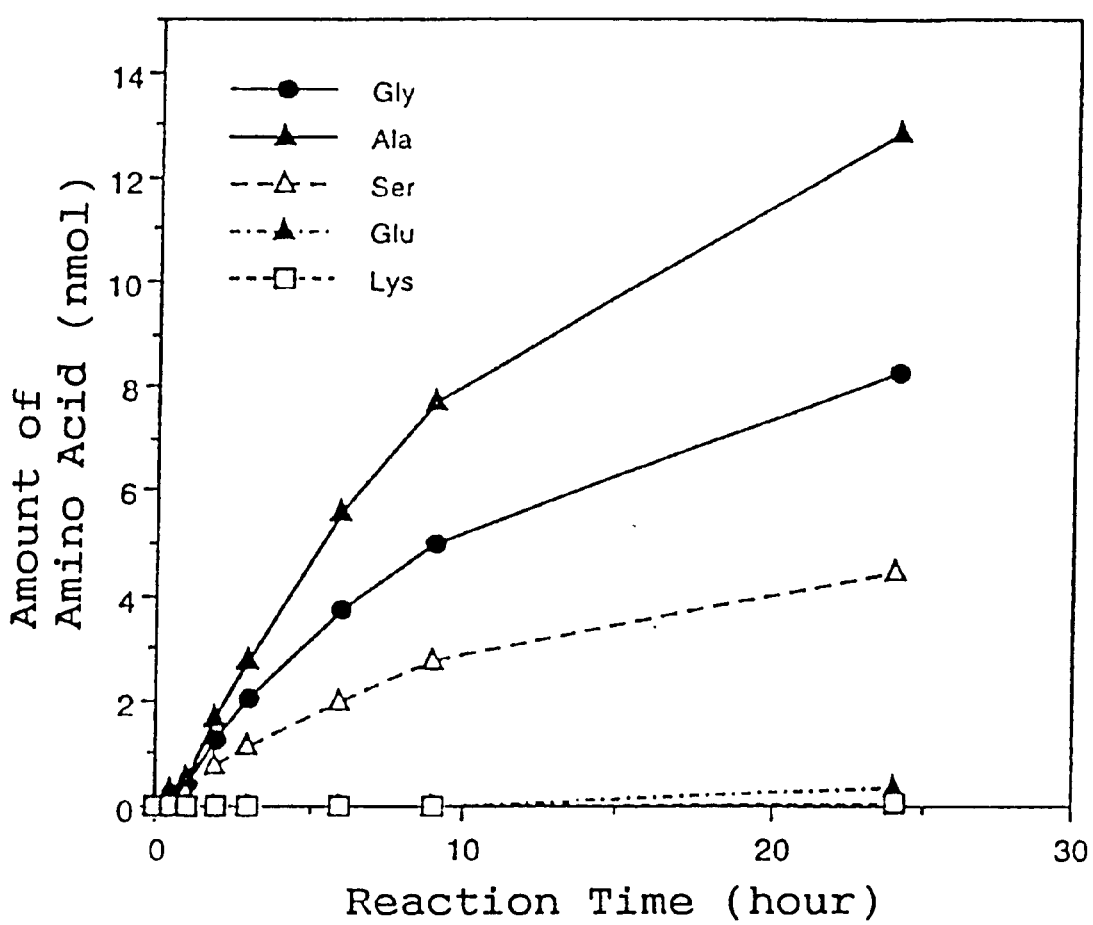
F I G. 1 1

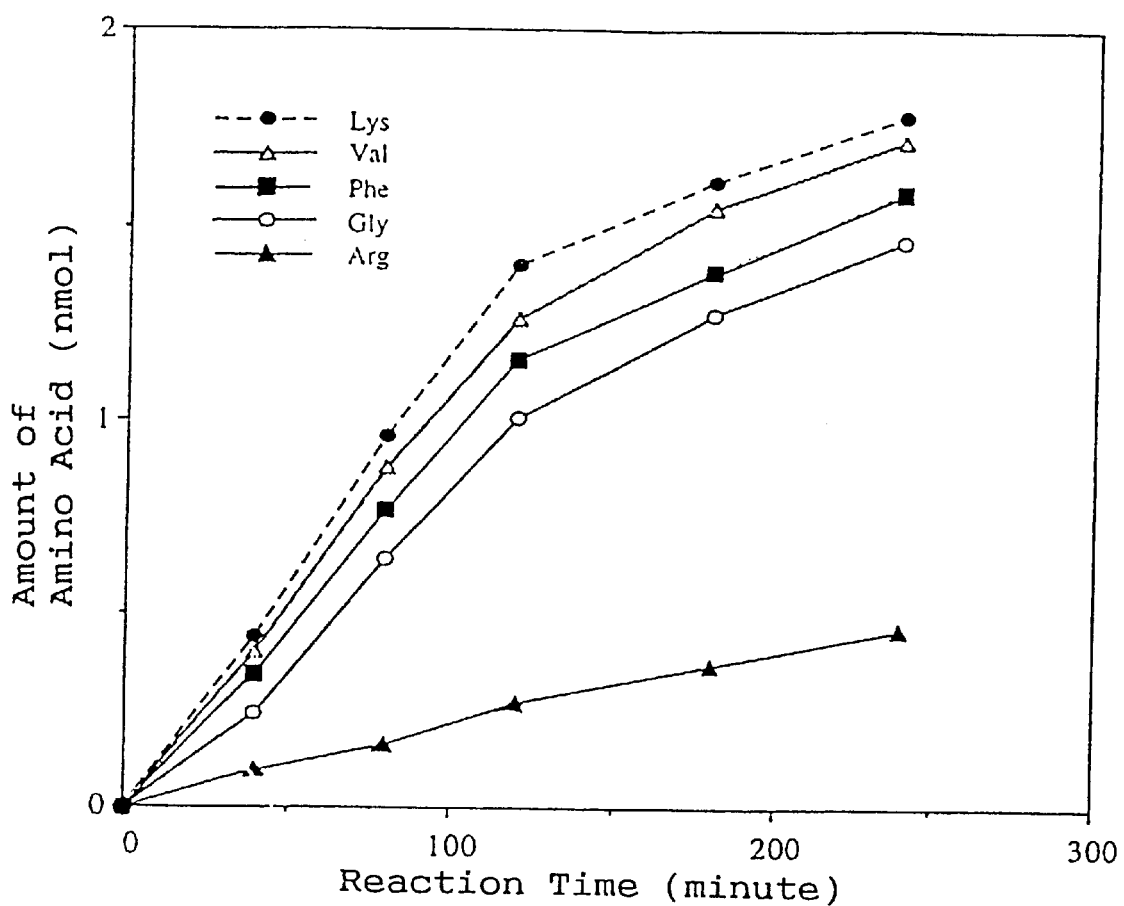
F I G. 1 2

SEQUENCE LISTING

<160> NUMBER OF SEQ ID NOS: 17

<210> SEQ ID NO 1
<211> LENGTH: 348
<212> TYPE: PRT
<213> ORGANISM: Pyrococcus furiosus

<400> SEQUENCE: 1

```
Met Val Asp Tyr Glu Leu Leu Lys Lys Val Val Glu Ala Pro Gly Val
  1               5                  10                  15

Ser Gly Tyr Glu Phe Met Gly Ile Arg Asp Val Val Ile Glu Glu Ile
             20                  25                  30

Lys Asp Tyr Val Asp Glu Val Asn Val Asp Lys Leu Gly Asn Val Ile
         35                  40                  45

Ala His Lys Lys Gly Glu Gly Pro Lys Val Met Ile Ala Ala His Met
     50                  55                  60

Asp Gln Ile Gly Leu Met Val Thr His Ile Glu Lys Asn Gly Phe Leu
 65                  70                  75                  80

Arg Val Ala Pro Ile Gly Gly Ile Asp Pro Arg Thr Leu Ile Ala Gln
                 85                  90                  95

Arg Phe Lys Val Trp Ile Asp Lys Gly Lys Phe Ile Tyr Gly Val Gly
                100                 105                 110

Gly Ser Val Pro Pro His Ile Gln Lys Pro Glu Asp Arg Lys Lys Ala
            115                 120                 125

Pro Asp Trp Asp Gln Ile Phe Ile Asp Ile Gly Ala Glu Ser Lys Glu
        130                 135                 140

Glu Ala Glu Glu Leu Gly Val Lys Ile Gly Thr Ile Val Thr Trp Asp
145                 150                 155                 160

Gly Arg Leu Glu Arg Leu Gly Lys His Arg Phe Val Ser Ile Ala Phe
                165                 170                 175
```

Asp Asp Arg Ile Ala Val Tyr Thr Leu Ile Glu Thr Ala Arg Gln Leu
            180                 185                 190

Gln Asp Thr Lys Ala Asp Ile Tyr Phe Val Ala Thr Val Gln Glu Glu
        195                 200                 205

Val Gly Leu Arg Gly Ala Arg Thr Ser Ala Phe Gly Ile Asn Pro Asp
    210                 215                 220

Tyr Gly Phe Ala Ile Asp Val Thr Ile Ala Ala Asp Val Pro Gly Thr
225                 230                 235                 240

Pro Glu His Lys Gln Val Thr Gln Leu Gly Lys Gly Thr Ala Ile Lys
                245                 250                 255

Ile Met Asp Arg Ser Val Ile Cys His Pro Thr Ile Val Arg Trp Met
                260                 265                 270

Glu Glu Leu Ala Lys Lys Tyr Glu Ile Pro Tyr Gln Trp Asp Ile Leu
            275                 280                 285

Leu Gly Gly Gly Thr Asp Ala Gly Ala Ile His Leu Thr Arg Ala Gly
        290                 295                 300

Val Pro Thr Gly Ala Val Ser Ile Pro Ala Arg Tyr Ile His Ser Asn
305                 310                 315                 320

Ala Glu Val Val Asp Glu Arg Asp Val Asp Ala Ser Val Lys Leu Met
                325                 330                 335

Val Lys Val Leu Glu His Ile His Glu Leu Lys Ile
            340                 345

<210> SEQ ID NO 2
<211> LENGTH: 1044
<212> TYPE: DNA
<213> ORGANISM: Pyrococcus furiosus

<400> SEQUENCE: 2
atggtggact atgagctttt aaaaaaggta gtagaggctc cgggagtttc aggatatgag      60
ttcatgggaa ttagagatgt cgttattgaa gagataaagg actatgtgga tgaagtaaat     120
gtagacaaac tcggaaacgt tattgctcac aagaaagggg aaggtccaaa agtaatgata     180
gcggcccata tggatcaaat tggactgatg gtcacgcata tagaaaagaa tggatttctc     240
agagttgctc caataggagg aatagatcca aggacattaa ttgctcagag gtttaaagtt     300
tggatagaca aaggaaagtt tatctacgga gttggaggta gtgttcctcc acacatacag     360
aagcctgaag ataggaagaa agctccagat tgggatcaga tattcataga cattggagca     420
gagagcaagg aagaggccga ggagttggga gtaaaaatag aacaatagt aacctgggat     480 gggagacttg agaggctggg aaacacagat tttgtcagca tagcatttga cgataggata     540
gctgtataca ctttaattga aactgcaaga cagcttcaag atacgaaggc agatatctac     600
tttgtggcca cagtgcagga ggaggttggg ttaagaggtg cgaggacaag tgcctttgga     660
attaatcccg attatggttt tgccattgat gttactatag ctgcagatgt accaggaaca     720
ccagagcaca agcaagttac tcaacttgga aagggcactg caatcaagat aatggatcgt     780
tcagtaatct gccatccaac aattgttagg tggatgaggg aactggcaaa agagtacgag     840
attccttacc agtgggatat tctgctggga ggaggtacag acgctggggc tattcactta     900
actagggctg gagttccaac aggtgctgta agtattcctg cacgatacat acactcaaat     960
gcagaggttg tagatgagag agacgttgat gcaagtgtaa agttgatggt aaaagttctt    1020
gaacatatac acgagctaaa gatt                                           1044

<210> SEQ ID NO 3

<211> LENGTH: 1247
<212> TYPE: DNA
<213> ORGANISM: Pyrococcus furiosus

<400> SEQUENCE: 3

```
gtagtttctc cttaaaagtc tcgcccaaaa tccttatata atgagaaaat aacacttaga      60
tgatcatcta aatgggggga ggaagatggt ggactatgag cttttaaaaa aggtagtaga     120
ggctccggga gtttcaggat atgagttcat gggaattaga gatgtcgtta ttgaagagat     180
aaaggactat gtggatgaag taatgtaga caaactcgga aacgttattg ctcacaagaa      240
aggggaaggt ccaaaagtaa tgatagcggc ccatatggat caaattggac tgatggtcac     300
gcatatagaa aagaatggat ttctcagagt tgctccaata ggaggaatag atccaaggac     360
attaattgct cagaggttta agtttggat agacaaagga aagtttatct acggagttgg     420
aggtagtgtt cctccacaca tacagaagcc tgaagatagg aagaaagctc cagattggga     480
tcagatattc atagacattg gagcagagag caaggaagag gccgaggagt tgggagtaaa     540
aataggaaca atagtaacct gggatgggag acttgagagg ctggggaaac acagatttgt     600
cagcatagca tttgacgata ggatagctgt atacacttta attgaaactg caagacagct     660
tcaagatacg aaggcagata tctactttgt ggccacagtg caggaggagg ttgggttaag     720
aggtgcgagg acaagtgcct ttggaattaa tcccgattat ggttttgcca ttgatgttac     780
tatagctgca gatgtaccag aacaccaga gcacaagcaa gttactcaac ttggaaaggg     840
cactgcaatc aagataatgg atcgttcagt aatctgccat ccaacaattg ttaggtggat     900
ggaggaactg gcaaagaagt acgagattcc ttaccagtgg gatattctgc tgggaggagg     960
tacagacgct ggggctattc acttaactag ggctggagtt ccaacaggtg ctgtaagtat    1020
tcctgcacga tacatacact caaatgcaga ggttgtagat gagagagacg ttgatgcaag    1080
tgtaaagttg atggtaaaag ttcttgaaca tatacacgag ctaaagattt aattactctc    1140
ttaccttatt ttttaggtga ttctggatga gggtattgaa agaatggaat gttcaagtta    1200
agcttgtaag aaccaaaaga ggagcaatac ttccccatga tagagct                   1247
```

<210> SEQ ID NO 4
<211> LENGTH: 12
<212> TYPE: PRT
<213> ORGANISM: Artificial Sequence
<220> FEATURE:
<223> OTHER INFORMATION: Xaa = N-pyroglutamyl-leucine
<220> FEATURE:
<223> OTHER INFORMATION: Description of Artificial Sequence: Neurotensin
      manufactured by Peptide Institute, Inc.

<400> SEQUENCE: 4

Xaa Tyr Glu Asn Lys Pro Arg Arg Pro Tyr Ile Leu
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Xaa = N-acetyl-serine
<220> FEATURE:
<223> OTHER INFORMATION: Description of Artificial Sequence: Alpha-MSH

<400> SEQUENCE: 5

Xaa Tyr Ser Met Glu His Phe Arg Trp Gly Lys Pro Val
 1               5                  10

```
<210> SEQ ID NO 6
<211> LENGTH: 5
<212> TYPE: PRT
<213> ORGANISM: Artificial Sequence
<220> FEATURE:
<223> OTHER INFORMATION: Xaa = N-acetyl-glycine
<220> FEATURE:
<223> OTHER INFORMATION: Description of Artificial Sequence: Artificial
      Peptide

<400> SEQUENCE: 6

Xaa Asp Val Glu Lys
 1               5

<210> SEQ ID NO 7
<211> LENGTH: 4
<212> TYPE: PRT
<213> ORGANISM: Artificial Sequence
<220> FEATURE:
<223> OTHER INFORMATION: Xaa = N-formyl-methionine
<220> FEATURE:
<223> OTHER INFORMATION: Description of Artificial Sequence:
      manufactured by BACHEM

<400> SEQUENCE: 7

Xaa Leu Phe Lys
 1

<210> SEQ ID NO 8
<211> LENGTH: 9
<212> TYPE: PRT
<213> ORGANISM: Artificial Sequence
<220> FEATURE:
<223> OTHER INFORMATION: Xaa = N-myristoyl-phenylalanine
<220> FEATURE:
<223> OTHER INFORMATION: Description of Artificial Sequence:
      manufactured by BACHEM

<400> SEQUENCE: 8

Xaa Ala Arg Lys Gly Ala Leu Arg Gln
 1               5

<210> SEQ ID NO 9
<211> LENGTH: 9
<212> TYPE: PRT
<213> ORGANISM: Artificial Sequence
<220> FEATURE:
<223> OTHER INFORMATION: Xaa = N-myristoyl-glycine
<220> FEATURE:
<223> OTHER INFORMATION: Description of Artificial Sequence: Artificial
      Peptide

<400> SEQUENCE: 9

Xaa Ala Gly Ala Ser Ala Glu Glu Lys
 1               5

<210> SEQ ID NO 10
<211> LENGTH: 348
<212> TYPE: PRT
<213> ORGANISM: Pyrococcus furiosus
<220> FEATURE:
<223> OTHER INFORMATION: Xaa = N-acetyl-methionine

<400> SEQUENCE: 10

Xaa Asp Asp Tyr Glu Leu Leu Lys Lys Val Val Glu Ala Pro Gly Val
 1               5                  10                  15

Ser Gly Tyr Glu Phe Met Gly Ile Arg Asp Val Val Ile Glu Glu Ile
                20                  25                  30
```

```
Lys Asp Tyr Val Asp Glu Val Asn Val Asp Lys Leu Gly Asn Val Ile
         35                  40                  45
Ala His Lys Lys Gly Glu Gly Pro Lys Val Met Ile Ala Ala His Met
     50                  55                  60
Asp Gln Ile Gly Leu Met Val Thr His Ile Glu Lys Asn Gly Phe Leu
 65                  70                  75                  80
Arg Val Ala Pro Ile Gly Gly Ile Asp Pro Arg Thr Leu Ile Ala Gln
                 85                  90                  95
Arg Phe Lys Val Trp Ile Asp Lys Gly Lys Phe Ile Tyr Gly Val Gly
                100                 105                 110
Gly Ser Val Pro Pro His Ile Gln Lys Pro Glu Asp Arg Lys Lys Ala
            115                 120                 125
Pro Asp Trp Asp Gln Ile Phe Ile Asp Ile Gly Ala Glu Ser Lys Glu
130                 135                 140
Glu Ala Glu Glu Leu Gly Val Lys Ile Gly Thr Ile Val Thr Trp Asp
145                 150                 155                 160
Gly Arg Leu Glu Arg Leu Gly Lys His Arg Phe Val Ser Ile Ala Phe
                165                 170                 175
Asp Asp Arg Ile Ala Val Tyr Thr Leu Ile Glu Thr Ala Arg Gln Leu
            180                 185                 190
Gln Asp Thr Lys Ala Asp Ile Tyr Phe Val Ala Thr Val Gln Glu Glu
        195                 200                 205
Val Gly Leu Arg Gly Ala Arg Thr Ser Ala Phe Gly Ile Asn Pro Asp
210                 215                 220
Tyr Gly Phe Ala Ile Asp Val Thr Ile Ala Ala Asp Val Pro Gly Thr
225                 230                 235                 240
Pro Glu His Lys Gln Val Thr Gln Leu Gly Lys Gly Thr Ala Ile Lys
                245                 250                 255
Ile Met Asp Arg Ser Val Ile Cys His Pro Thr Ile Val Arg Trp Met
            260                 265                 270
Glu Glu Leu Ala Lys Lys Tyr Glu Ile Pro Tyr Gln Trp Asp Ile Leu
        275                 280                 285
Leu Gly Gly Gly Thr Asp Ala Gly Ala Ile His Leu Thr Arg Ala Gly
290                 295                 300
Val Pro Thr Gly Ala Val Ser Ile Pro Ala Arg Tyr Ile His Ser Asn
305                 310                 315                 320
Ala Glu Val Val Asp Glu Arg Asp Val Asp Ala Ser Val Lys Leu Met
                325                 330                 335
Val Lys Val Leu Glu His Ile His Glu Leu Lys Ile
            340                 345

<210> SEQ ID NO 11
<211> LENGTH: 1044
<212> TYPE: DNA
<213> ORGANISM: Pyrococcus furiosus

<400> SEQUENCE: 11
atggatgact atgagctttt aaaaaaggta gtagaggctc cgggagtttc aggatatgag      60
ttcatgggaa ttagagatgt cgttattgaa gagataaagg actatgtgga tgaagtaaat     120
gtagacaaac tcggaaacgt tattgctcac aagaaggggg aaggtccaaa agtaatgata     180
gcggcccata tggatcaaat tggactgatg gtcacgcata tagaaaagaa tggatttctc     240
agagttgctc caataggagg aatagatcca aggacattaa ttgctcagag gtttaaagtt     300
```

-continued

| | |
|---|---|
| tggatagaca aaggaaagtt tatctacgga gttggaggta gtgttcctcc acacatacag | 360 |
| aagcctgaag ataggaagaa agctccagat tgggatcaga tattcataga cattggagca | 420 |
| gagagcaagg aagaggccga ggagttggga gtaaaaatag gaacaatagt aacctgggat | 480 |
| gggagacttg agaggctggg gaaacacaga tttgtcagca tagcatttga cgataggata | 540 |
| gctgtataca ctttaattga aactgcaaga cagcttcaag atacgaaggc agatatctac | 600 |
| tttgtggcca cagtgcagga ggaggttggg ttaagaggtg cgaggacaag tgcctttgga | 660 |
| attaatcccg attatggttt tgccattgat gttactatag ctgcagatgt accaggaaca | 720 |
| ccagagcaca agcaagttac tcaacttgga aagggcactg caatcaagat aatggatcgt | 780 |
| tcagtaatct gccatccaac aattgttagg tggatggagg aactggcaaa gaagtacgag | 840 |
| attccttacc agtgggatat tctgctggga ggaggtacag acgctgggc tattcactta | 900 |
| actagggctg gagttccaac aggtgctgta agtattcctg cacgatacat acactcaaat | 960 |
| gcagaggttg tagatgagag agacgttgat gcaagtgtaa agttgatggt aaaagttctt | 1020 |
| gaacatatac acgagctaaa gatt | 1044 |

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12

| | |
|---|---|
| gctcatagtc atccatcttc ctcc | 24 |

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13

| | |
|---|---|
| tgattacgcc tagcttacat | 20 |

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14

| | |
|---|---|
| ctaaatgggg ggatccagat ggatgac | 27 |

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15

| | |
|---|---|
| agctctatca tggggaagta ttgc | 24 |

-continued

```
<210> SEQ ID NO 16
<211> LENGTH: 151
<212> TYPE: PRT
<213> ORGANISM: Artificial Sequence
<220> FEATURE:
<223> OTHER INFORMATION: Description of Artificial Sequence: superoxide
      dismutase

<400> SEQUENCE: 16

Ala Thr Lys Ala Val Cys Val Leu Lys Gly Asp Gly Pro Val Gln Gly
1               5                   10                  15

Thr Ile His Phe Glu Ala Lys Gly Asp Thr Val Val Val Thr Gly Ser
            20                  25                  30

Ile Thr Gly Leu Thr Glu Gly Asp His Gly Phe His Val His Gln Phe
        35                  40                  45

Gly Asp Asn Thr Gln Gly Cys Thr Ser Ala Gly Pro His Phe Asn Pro
    50                  55                  60

Leu Ser Lys Lys His Gly Gly Pro Lys Asp Glu Arg His Val Gly
65                  70                  75                  80

Asp Leu Gly Asn Val Thr Ala Asp Lys Asn Gly Val Ala Ile Val Asp
                85                  90                  95

Ile Val Asp Pro Leu Ile Ser Leu Ser Gly Glu Tyr Ser Ile Ile Gly
            100                 105                 110

Arg Thr Met Val Val His Glu Lys Pro Asp Asp Leu Gly Arg Gly Gly
        115                 120                 125

Asn Glu Glu Ser Thr Lys Thr Gly Asn Ala Gly Ser Arg Leu Ala Cys
    130                 135                 140

Gly Val Ile Gly Ile Ala Lys
145                 150

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: amino
      terminal of S-reduced chicken egg white lysozyme
      manufactured by Wako Pure Chemical Industries

<400> SEQUENCE: 17

Lys Val Phe Gly Arg
1               5
```

AMINO-TERMINAL DEBLOCKING ENZYME

This application is the national phase under 35 U.S.C. §371 of prior PCT International Application No. PCT/JP97/02121 which has an International filing date of Jun. 19, 1997 which designated the United States of America.

TECHNICAL FIELD

The present invention pertains to an amino terminal protecting group-releasing enzyme which has an activity for releasing a protecting group which is present at an amino terminal of a protein or a peptide. The present invention also pertains to a DNA encoding the above amino terminal protecting group-releasing enzyme. The present invention also pertains to a method for producing the above amino terminal protecting group-releasing enzyme by means of a genetic recombinant technique. The present invention also pertains to a method for removing an amino terminal protecting group by using the above amino terminal protecting group-releasing enzyme. The present invention further pertains to a method for analyzing an amino acid sequence by means of the above removal method. The present invention further pertains to a kit for use in analyzing an amino acid sequence, the kit comprising the above amino terminal protecting group-releasing enzyme. The present invention further pertains to an antibody or a fragment thereof specifically binding to the above amino terminal protecting group-releasing enzyme, or a functional equivalent thereof. The present invention further pertains to a synthesized oligonucleotide probe or a synthesized oligonucleotide primer which is capable of hybridizing to the above DNA, respectively.

BACKGROUND ART

The determination of the amino terminal amino acid sequences of proteins and peptides is an essential analysis for their identification or confirmation.

However, 60% or more of the soluble proteins derived from eukaryote reportedly have the α-amino group at their amino terminal blocked by either an acetyl group or another protecting group; and in the Edman degradation method, a well-established commonly used method for. analyzing an amino acid sequence from the amino terminal, proteins and peptides of which amino terminal is blocked by a protecting group cannot be analyzed.

As the protecting groups blocking the amino terminal of proteins and peptides, formyl group, acetyl group, myristoyl group, pyroglutamyl group, dimethyl group, glucuronyl group, glycosyl group and trimethyl group have been reported. As the method for analyzing an amino terminal amino acid sequence for such blocked proteins, there can be employed the Edman degradation method applied after removing a protecting group.

The removal of protecting groups includes a method using an enzyme and a chemical method. However, an enzymatic method has a drawback of a lack of versatility, since different enzymes are used depending on the kinds of protecting groups to be removed. For example, acylamino acid releasing enzyme is used in the case of acetyl groups, and pyroglutamyl peptidase in the case of pyroglutamyl groups. Also, as to chemical method, no versatile methods have been developed to date. In addition, because there is no known method of identifying the protecting group when the amino terminal is blocked thereby, when the protecting group is actually removed, there are no other alternatives except that a number of methods for removing protecting group depending on respective protecting groups are attempted one by one. Furthermore, since there is no effective method for removing a protecting group available for the proteins and peptides blocked with myristoyl group, it is impossible to determine their amino acid sequences from the amino terminal.

Incidentally, as the peptidases isolated from *Pyrococcus furiosus*, the peptidases acting on an amino terminal portion of a peptide, there have been known an aminopeptidase (Japanese Patent Laid-Open No. Hei 6-319566), a pyroglutamyl peptidase (Japanese Patent Laid-Open No. Hei 7-298881), and a methionine aminopeptidase (Japanese Patent Laid-Open No. Hei 8-9979). Among these peptidases, the pyroglutamyl peptidase possesses an activity for releasing of the amino terminal pyroglutamyl group, but does not act on other protecting groups, e.g., acetyl groups. In addition, the other two kinds of enzymes both cannot act on amino terminal blocked by protecting groups.

As described above, the existing method for analyzing amino terminal amino acid sequence has the drawback of a lack of versatility when applied to proteins and peptides of which amino terminal is blocked by protecting groups.

DISCLOSURE OF INVENTION

Accordingly, an object of the present invention is to provide an amino terminal protecting group-releasing enzyme, the enzyme exhibiting an amino terminal group-releasing activity for two or more protecting groups, or a functional equivalent thereof; a DNA encoding the above enzyme; a method for producing the above enzyme; a method for removing an amino terminal protecting group comprising acting with the above enzyme; a method for analyzing an amino acid sequence by using the above method; and a kit for use in analyzing an amino acid sequence, the kit comprising the above enzyme. A further object of the present invention is to provide an antibody or a fragment thereof specifically binding to the above amino terminal protecting group-releasing enzyme, or a functional equivalent thereof; and a synthesized oligonucleotide probe or a synthesized oligonucleotide primer which is capable of hybridizing to the above DNA, respectively.

The present inventors have screened cosmid protein libraries from *Pyrococcus furiosus*, and have obtained a cosmid clone expressing an activity for releasing a protecting group at an amino terminal. The present inventors have isolated a gene of an amino terminal protecting group-releasing enzyme contained in this clone, and have determined its base sequence. In addition, the present inventors have constructed a recombinant plasmid for mass-expressing the enzyme in microorganisms. As a result, the present inventors have succeeded in producing the enzyme and have clarified various enzymological properties of the enzyme. Furthermore, the present inventors have found that the enzyme possesses an activity for releasing a plurality of amino terminal protecting groups such as typically an acetyl group. In addition, the present inventors have succeeded in preparing the functional equivalent of the enzyme. The present invention has been thus completed.

Specifically, in sum, the present invention pertains to:

[1] an amino terminal protecting group-releasing enzyme characterized in that the enzyme possesses an activity for releasing a protecting group by acting on a peptide of which amino terminal is blocked by the protecting group (hereinafter abbreviated as a term "amino terminal protecting group-releasing activity"), and exhibits the activity for two or more protecting groups;

[2] the enzyme according to the above item [1], wherein the enzyme exhibits an amino terminal protecting group-releasing activity for at least two or more of protecting groups selected from the group consisting of acetyl group, pyroglutamyl group, formyl group and myristoyl group;

[3] the enzyme according to the above claim 1 or 2, wherein the enzyme further possesses an amino peptidase activity;

[4] the enzyme according to any one of the above items [1] to [3], wherein the enzyme possesses the following physicochemical properties:
  (1) optimal temperature: 75° to 95° C. at a pH of 7.6;
  (2) optimal pH: a pH of 6.5 to 9.5; and
  (3) effects of various reagents:
    the activity being inhibited by amastatin, and enhanced by $CoCl_2$.

[5] the enzyme according to any one of the above items [1] to [4], wherein the enzyme comprises an entire sequence of the amino acid sequence as shown by SEQ ID NO: 1 in Sequence Listing, or a partial sequence thereof, and wherein the enzyme exhibits an amino terminal protecting group-releasing activity;

[6] a functional equivalent of the enzyme according to the above item [5], wherein the functional equivalent has an amino acid sequence resulting from at least one of deletion, insertion, addition or substitution of one or more amino acid residues in the amino acid sequence as shown by SEQ ID NO: 1 in Sequence Listing, and wherein the functional equivalent exhibits an amino terminal protecting group-releasing activity;

[7] the functional equivalent according to the above item [6], wherein an amino terminal of the functional equivalent is blocked by a protecting group;

[8] the functional equivalent according to the above item [7], wherein the protecting group is acetyl group;

[9] the functional equivalent according to the above item [8], wherein the functional equivalent has the amino acid sequence as shown by SEQ ID NO: 10 in Sequence Listing;

[10] a DNA encoding the amino terminal protecting group-releasing enzyme according to any one of the above items [1] to [4];

[11] a DNA encoding a polypeptide comprising an entire sequence of the amino acid sequence as shown by SEQ ID NO: 1 in Sequence Listing, or a partial sequence thereof, wherein the polypeptide exhibits an amino terminal protecting group-releasing activity;

[12] a DNA encoding a polypeptide exhibiting an amino terminal protecting group-releasing activity, wherein the DNA comprises an entire sequence of the DNA as shown by SEQ ID NO: 2 in Sequence Listing, or a partial sequence thereof;

[13] a DNA encoding a protein resulting from at least one of deletion, insertion, addition or substitution of one or more amino acid residues in the amino acid sequence as shown by SEQ ID NO: 1 in Sequence Listing, and wherein the protein exhibits an amino terminal protecting group-releasing activity;

[14] the DNA according to the above item [13], wherein the DNA has the base sequence as shown by SEQ ID NO: 11 in Sequence Listing;

[15] a DNA encoding a protein exhibiting an amino terminal protecting group-releasing activity, wherein the DNA is capable of hybridizing to the DNA according to any one of the above items [10] to [14];

[16] a recombinant DNA comprising the DNA according to any one of the above items [10] to [14];

[17] an expression vector for a microorganism, an animal cell or a plant cell as a host cell, wherein the recombinant DNA according to the above item [16] is inserted in the expression vector;

[18] a transformant which is transformed with the expression vector according to the above item [17];

[19] a method for producing an amino terminal protecting group-releasing enzyme or a functional equivalent thereof, comprising the steps of culturing the transformant according to the above item [18], and collecting from a culture a protein possessing an amino terminal protecting group-releasing activity or a polypeptide possessing an activity functionally equivalent to that of the protein;

[20] a method for removing an amino terminal protecting group, comprising the steps of subjecting a peptide of which amino terminal is blocked by a protecting group to a reaction with the amino terminal protecting group-releasing enzyme according to any one of the above items [1] to [9] or a functional equivalent thereof to release the protecting group at the amino terminal;

[21] a method for analyzing an amino acid sequence of a peptide of which amino terminal is blocked by a protecting group, comprising the steps of releasing the protecting group by the method for removing according to the above items [18], and then subjecting the resulting peptide to an amino acid sequence analysis;

[22] a kit for use in analyzing an amino acid sequence of a peptide of which amino terminal is blocked by a protecting group, characterized in that the kit comprises the amino terminal protecting group-releasing enzyme according to any-one of the above items [1] to [9] or a functional equivalent thereof;

[23] an antibody or a fragment thereof which specifically binds to the amino terminal protecting group-releasing enzyme according to any one of the above items [1] to [9] or a functional equivalent thereof; and

[24] a synthesized oligonucleotide probe or a synthesized oligonucleotide primer, which is capable of hybridizing to the DNA according to any one of the above items [10] to [15].

BRIEF DESCRIPTION OF THE DRAWINGS

FIG. 1 shows a restriction endonuclease map of a plasmid pDAP3.

FIG. 2 shows a restriction endonuclease map of a plasmid pDAP.

FIG. 3 is a graph showing an optimal temperature of an amino terminal protecting group-releasing enzyme of the present invention.

FIG. 5 is a graph showing a temperature stability of an amino terminal protecting group-releasing enzyme of the present invention at 75° C. In the figure, closed circles indicate data taken in a buffer containing 0.1 mM $CoCl_2$; and open circles indicate data taken in a buffer without containing $CoCl_2$.

FIG. 6 is a graph showing an action of an amino terminal protecting group-releasing enzyme in the present invention with the passage of time on neurotensin.

FIG. 7 is a graph showing an action of an amino terminal protecting group-releasing enzyme in the present invention with the passage of time on α-MSH.

FIG. 8 is a graph showing an action of an amino terminal protecting group-releasing enzyme in the present invention with the passage of time on Ac-Gly-Asp-Val-Glu-Lys (SEQ ID NO:6).

FIG. 9 is a graph showing an action of an amino terminal protecting group-releasing enzyme in the present invention with the passage of time on For-Met-Leu-Phe-Lys (SEQ ID NO:7).

FIG. 11 is a graph showing an action of an amino terminal protecting group-releasing enzyme in the present invention with the passage of time on Myr-Gly-Ala-Gly-Ala-Ser-Ala-Glu-Glu-Lys (SEQ ID NO:9).

FIG. 12 is a graph showing an action of an amino terminal protecting group-releasing enzyme in the present invention with the passage of time on a reduced lysozyme.

BEST MODE FOR CARRYING OUT THE INVENTION

Figure 4:
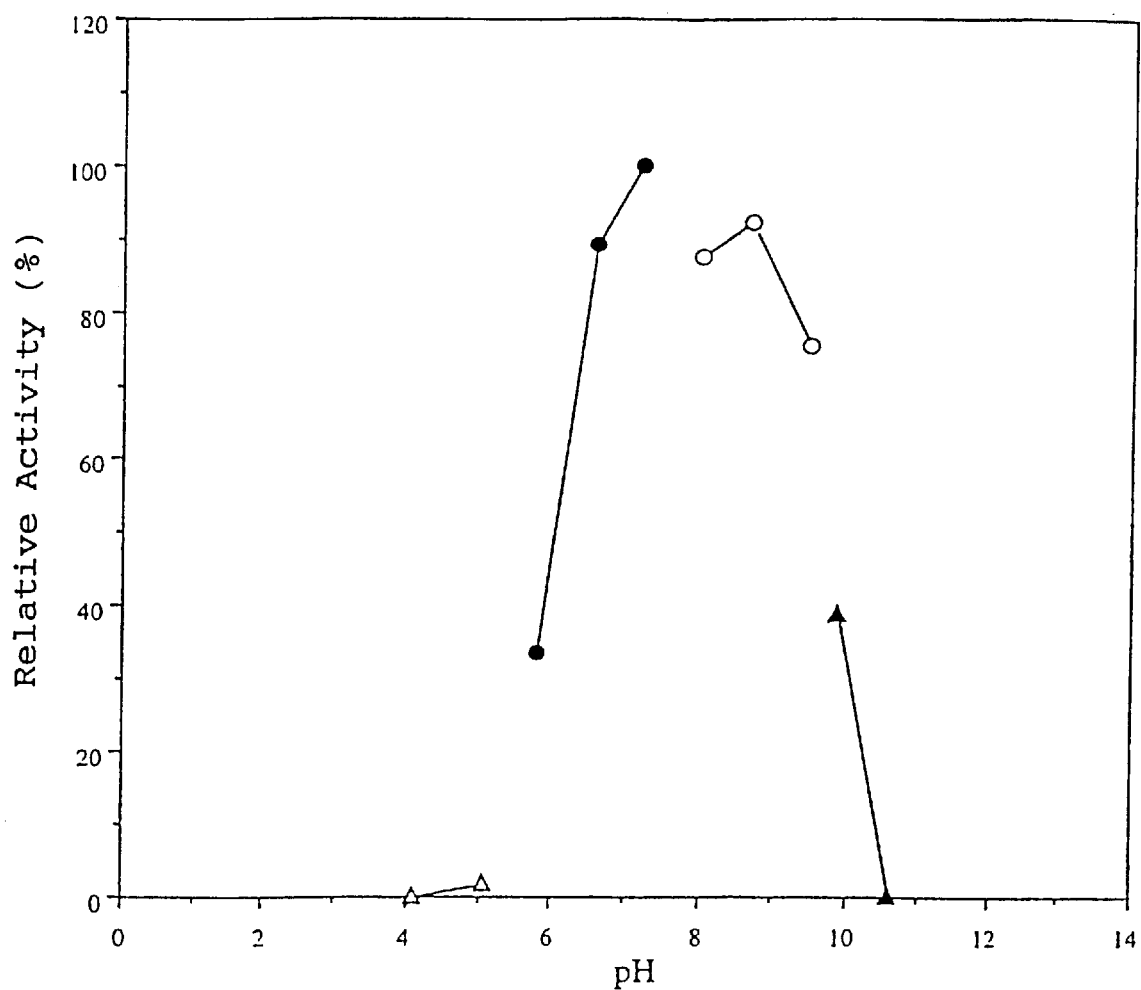
FIG. 4 is a graph showing an optimal pH of an amino terminal protecting group-releasing enzyme of the present invention. In the figure, open triangles indicate data when using sodium acetate buffer; closed circles indicate data when using PIPES-Na buffer; open circles indicate data when using sodium borate buffer; and closed triangles indicate data when using disodium hydrogenphosphate-sodium hydroxide buffer.

1. Amino Terminal Protecting Group-Releasing Enzyme of Present Invention

The amino terminal protecting group-releasing enzyme of the present invention is characterized in that the enzyme possesses an activity for releasing a protecting group by acting on a peptide of which amino terminal is blocked by the protecting group (amino terminal protecting group-releasing activity), and exhibits the activity for two or more kinds of protecting groups.

The term "peptide" as used herein, refers to a substrate in which two or more amino acids are linked via peptide bonds, and includes those described as "proteins".

The protecting groups which are present at the amino terminal of such peptide include acetyl group, pyroglutamyl group, formyl group and myristoyl group. The amino terminal protecting group-releasing enzyme of the present invention possesses an activity for releasing at least two kinds of these protecting groups from the amino terminal of the substrate peptide. The amino terminal protecting group-releasing activity as described above can be measured by the method described below, using a synthetic peptide of which amino terminal is blocked by any one of the above-mentioned protecting groups, or the like, as a substrate.

The amino terminal protecting group-releasing enzyme of the present invention includes an enzyme possessing an amino terminal protecting group-releasing activity; and an enzyme possessing an amino terminal protecting group-releasing activity and an aminopeptidase activity for sequentially releasing amino acids from the amino terminal of a peptide. Specifically, there can be included as an example, an enzyme comprising the amino acid sequence as shown by SEQ ID NO: 1 in Sequence Listing. When an enzyme further possesses an aminopeptidase activity, analysis of the amino acid sequence of the peptide can be carried out without using in combination with other method of peptide amino terminal degradation. The aminopeptidase activity as described above can be measured by a conventionally known method [*Arch. Biochem. Biophys.*, 274, pp. 241–250 (1989)].

One example of the enzymes possessing an amino terminal protecting group-releasing activity and an aminopeptidase activity concretely includes an enzyme comprising the amino acid sequence as shown by SEQ ID NO: 1 in Sequence Listing. The enzyme of the present invention may have its amino terminal in a free form or have its amino acid terminal blocked by a protecting group. It is therefore understood that unless specified otherwise, the amino terminal of the enzyme of the present invention includes either one of forms. Therefore, enzymes having the sequence as shown by SEQ ID NO: 1, and having an amino terminal blocked by a protecting group, such as an acetyl group, are also included in the scope of the present invention, although SEQ ID NO: 1 shows the sequence where the amino terminal is in a free form.

The amino terminal protecting group-releasing enzyme of the present invention can be produced by methods, for example, 1) a purification from a culture of a microorganism for producing the enzyme of the present invention, and 2) a purification from a culture of a transformant containing a DNA encoding the enzyme of the present invention.

1) Purification from Culture of Microorganism for Producing Enzyme of Present Invention The microorganism for producing the enzyme of the present invention can be obtained by screening with enzyme activity as an index. Methods for detecting an enzyme activity include those wherein release of a protecting group from the substrate is confirmed by high-performance liquid chromatography, amino acid analysis, mass spectrometric analysis, etc., using an amino acid or peptide of which amino terminal is blocked by a protecting group as a substrate. It is also possible to use synthetic substrates prepared by adding an appropriate coloring group or fluorescent group to an amino acid blocked by a protecting group.

By culturing a microorganism confirmed a production of an amino terminal protecting group-releasing enzyme as described above, the enzyme can be produced. Cultivation of a microorganism may be carried out under conditions suitable for the growth of the microorganism, preferably under conditions that induce the amount of expression of the desired enzyme. The desired enzyme thus produced in cells or culture broth can be purified by commonly used methods of enzyme purification.

A microorganism for producing the enzyme of the present invention, the microorganism being selected by the above screening, includes *Pyrococcus furiosus* DSM 3638.

The method for producing the enzyme of the present invention will be described by taking *Pyrococcus furiosus* DSM 3638 as an example, without intending to limit the method thereto. Incidentally, *Pyrococcus furiosus* DSM 3638 is a strain which can be made available by Deutsch Sammlung von Mikroorganismen und Zellkulturen und GmbH.

In the cultivation of the strain, methods commonly used for cultivation of hyperthermostable microorganisms can be utilized, and any nutrients can be added to the culture medium, as long as they are utilizable by the strain. As carbon sources, there can be used, for example, starch; as nitrogen sources, there can be used, for example, trypton, peptone and yeast extract. To the culture may be added metal salts, such as magnesium salts, sodium salts and iron salts as a trace element. It is also advantageous to use artificial seawater in the preparation of the culture. The culture is also desirably transparent one without containing solid sulfur. By use of the culture described above, the cell growth can be easily monitored by measurement of culture broth turbidity. Although this cultivation may be achieved by standing culture or spinner culture, for example, a method of dialytic culture can be employed, as described in *Applied and Environmental Microbiology*, 55, pp. 2086–2088 (1992). In general, the cultivation temperature is preferably around 95°

C., and an amino terminal protecting group-releasing enzyme is usually accumulated in considerable amounts in the culture in about 16 hours. It is preferable that the cultivation conditions are thus set to maximize the amount of production of amino terminal protecting group-releasing enzyme, depending on the strain and culture medium composition used.

When collecting the amino terminal protecting group-releasing enzyme, cells are harvested from the culture broth by, for example, centrifugation, filtration, etc., and subsequently disrupting the obtained cells to prepare a crude enzyme solution. As methods for disrupting cells, those methods having extraction effect of the desired enzyme may be selected out of ultrasonic disruption, bead disruption, lytic enzyme treatment, etc. When the enzyme is secreted in the culture broth, it is concentrated by ammonium sulfate salting-out, ultrafiltration, etc., to use the resulting concentrate as a crude enzyme solution. When isolating the amino terminal protecting group-releasing enzyme from the crude enzyme solution thus obtained, conventional methods for use in enzyme purification can be employed. For example, an ammonium sulfate salting-out treatment, ion exchange chromatography, hydrophobic chromatography, gel filtration chromatography, etc. can be used in combination.

2) Purification from Culture of Transformant Comprising DNA Encoding Enzyme of Present Invention A DNA encoding the enzyme according to the present invention can be obtained by screening of gene libraries of appropriate microorganisms. The microorganisms can be found by screening with an enzyme activity as an index.

More specifically, for example, a desired DNA can be obtained by screening from cosmid libraries of genome of bacteria belonging to the genus *Pyrococcus furiosus*, such as *Pyrococcus furiosus*. As *Pyrococcus furiosus*, *Pyrococcus furiosus* DSM 3638 can be used.

In addition, as to methods of cloning of a desired DNA from such microorganisms, preparation and cultivation of a transformant comprising a DNA encoding the enzyme of the present invention, and purification of a desired protein from the resulting culture, conventionally known methods can be employed therefor. The production method of the present invention will be described below by taking *Pyrococcus furiosus* DSM 3638 as an example, without intending to limit the method thereto.

The cosmid libraries for genome of *Pyrococcus furiosus* can be prepared by partially digesting *Pyrococcus furiosus* genomic DNA with a restriction enzyme Sau3AI (manufactured by Takara Shuzo Co., Ltd.), introducing the resulting DNA into triple helix cosmid vector (manufactured by Stratagene), and packaging into a lambda phage particle by means of in vitro packaging method. Thereafter, a clone comprising a DNA for the enzyme can be obtained by transforming a suitable *Escherichia coli*, such as *Escherichia coli* DH5αMCR (manufactured by BRL) using the resulting libraries, and assaying the resulting transformant for its enzyme activity in connection with the present invention.

Having remarked on the fact that an enzyme produced by *Pyrococcus furiosus* as a material possesses a high thermostability, the present inventors have combined processes for individually culturing transformants obtained using the cosmid library, and preparing lysates containing only thermostable proteins from the cells obtained, in screening the above enzyme activity. The series of lysates are named as a cosmid protein library. By using the cosmid protein library for detecting an enzyme activity, the detection sensitivity increases as compared to that of the method using a transformant colony, and harmful influences of background levels and an inhibition of enzyme activity by host-derived proteins etc. can be removed by thermal denaturation procedures.

Specifically, transformants obtained using a cosmid library are first cultured; the cells obtained are heat-treated (100° C., 10 minutes), ultrasonicated, and re-heat-treated (100° C., 10 minutes), followed by centrifugation to recover a supernatant (lysate), to prepared a cosmid protein library.

Next, each lysate contained in the library is examined whether or not a peptidase activity is present to carry out screening for peptidase-expressing clones. A synthetic peptide, an amino acid-4-methylcoumaryl-7-amide (hereinafter referred to as amino acid-MCA), can be used as substrates in a detection of peptidase activity, and useful amino acid-MCAs include for instance, Met-MCA, Leu-MCA, Ala-MCA, and His-MCA (manufactured by Peptide Institute, Inc.). The lysates found to possess peptidase activity can be further examined whether or not an amino terminal protecting group-releasing activity is present, using α-MSH (α-melanocyte stimulating hormone, manufactured by Peptide Institute, Inc.), a peptide of which amino terminal is blocked by an acetyl group as a substrate, by which a cosmid clone containing a DNA that expresses a protecting group-releasing activity can be obtained.

Further, a cosmid prepared from the cosmid clone thus obtained may be digested with appropriate restriction endonucleases to fragmentate to yield recombinant plasmids inserted with the respective fragments. Next, a recombinant plasmid containing a DNA encoding the desired enzyme can be obtained by examining the transformant obtained by introducing the plasmid into an appropriate microorganism for a Met-MCA decomposing activity.

A cosmid prepared from the above cosmid clone can be digested with BamHI (manufactured by Takara Shuzo Co., Ltd.), and the DNA fragment obtained can be inserted into the BamHI site of the plasmid vector pUC18 (manufactured by Takara Shuzo Co., Ltd.) to prepare a recombinant plasmid. A plasmid containing the desired DNA can be obtained by culturing *Escherichia coli* JM109 (manufactured by Takara Shuzo Co., Ltd.) in which the plasmid is introduced, and subsequently examining a peptidase activity of the lysate prepared from the cells obtained. The plasmid is named as a plasmid pDAP1.

Next, a recombinant plasmid can be prepared by digesting the above plasmid pDAP1 with EcoRI (manufactured by Takara Shuzo Co., Ltd.) and performing self-ligation. A plasmid containing the desired DNA can be obtained by confirming a peptidase activity of the lysate, prepared from the cells obtained by culturing *Escherichia coli* JM109 in which the plasmid is introduced. The plasmid is named as a plasmid pDAP2.

Furthermore, DNA fragments without containing the amino terminal protecting group-releasing enzyme gene can be removed from the above plasmid pDAP2 as described below. Specifically, a DNA fragment of about 1.7 kb resulting from digestion of the above plasmid pDAP2 with SacI (manufactured by Takara Shuzo Co., Ltd.) is inserted into the SacI site of a plasmid vector pUC18 (manufactured by Takara Shuzo Co., Ltd.) and introduced to *Escherichia coli* JM109. The peptidase activity of lysates prepared from the transformants obtained is determined, and a plasmid is prepared from a transformant exhibiting the activity. The plasmid is named as a plasmid pDAP3. FIG. 1 shows its restriction endonuclease map. In the figure, the bold solid line indicates a DNA insert in the plasmid vector pUC18.

Furthermore, DNA fragments without containing the amino terminal protecting group-releasing enzyme gene can be removed from the above plasmid pDAP3 as described below. Specifically, a SnaBI-SacI DNA fragment of about 1.2 kb resulting from digestion of the above plasmid pDAP3 with SnaBI (manufactured by Takara Shuzo Co., Ltd.) and SacI (manufactured by Takara Shuzo Co., Ltd.) is inserted into the SmaI-SacI site of a plasmid vector pUC19 and introduced to *Escherichia coli* JM109. The peptidase activity of the lysates prepared from the transformants obtained is determined. Further, the lysate activity for releasing an acetyl group from the amino terminal is then confirmed using α-MSH as a substrate, and a plasmid is prepared from a transformant exhibiting such an activity. The plasmid is named as a plasmid pDAP. FIG. 2 shows its restriction endonuclease map. In the figure, the bold solid line indicates the DNA insert in the plasmid vector pUC19. The *Escherichia coli* JM109 in which the plasmid PDAP is introduced is named as *Escherichia coli* JM109/pDAP, has been deposited under accession number FERM BP-5804 with the National Institute of Bioscience and Human-Technology, Agency of Industrial Science and Technology, Ministry of International Trade and Industry, of which the address is 1–3, Higashi 1-chome, Tsukuba-shi, Ibaraki-ken 305 Japan (date of original deposit: Mar. 29, 1996; transfer to international deposit: Jan. 30, 1997).

The base sequence of the DNA fragment derived from *Pyrrococcus furiosus* contained in the above plasmid pDAP can be determined by using known methods, such as dideoxy method.

The base sequence of the DNA fragment of about 1.2 kb inserted in the plasmid pDAP is shown by SEQ ID NO: 3 in Sequence Listing. The base sequence of the open reading frame in the sequence is shown by SEQ ID NO: 2 in Sequence Listing. Namely, SEQ ID NO: 2 in Sequence Listing is an example of base sequence of the amino terminal protecting group-releasing enzyme gene obtained by the present invention. The amino acid sequence of the amino terminal protecting group-releasing enzyme of the present invention as deduced from the base sequence shown by SEQ ID NO: 2 is shown by SEQ ID NO: 1. Namely, SEQ ID NO: 1 in Sequence Listing is an example of an amino acid sequence of the amino terminal protecting group-releasing enzyme gene obtained by the present invention.

The amino terminal protecting group-releasing enzyme of the present invention can be obtained using *Escherichia coli* JM109/pDAP, in which the plasmid pDAP obtained as described above is introduced.

Specifically, the amino terminal protecting group-releasing enzyme can be expressed in the cell culture by culturing *Escherichia coli* JM109/pDAP under conventional culturing conditions, e.g., culturing in an LB medium (10 g/l trypton, 5 g/l yeast extract, 5 g/l NaCl, pH 7.2) containing 100 µg/ml ampicillin at 37° C.

After completion of the cultivation, cells are harvested, and then the harvested cells are heat-treated at 100° C. for 10 minutes. A crude enzyme solution is obtained as a supernatant, the supernatant resulting from ultrasonication of the heat-treated cells, and then centrifugation of the ultrasonicated cells. The amino terminal protecting group-releasing enzyme can be purified by using a combination of methods conventionally used for enzyme purification, such as denaturation treatment of contaminated proteins by heat treatment at 100° C. for 10 minutes, gel filtration chromatography and ion exchange chromatography.

The enzymochemical and physicochemical properties of the amino terminal protecting group-releasing enzyme of the present invention as obtained from *Escherichia coli* JM109/pDAP by the method described above are shown below.

(1) Action

The enzyme of the present invention releases at least acetyl group, pyroglutamyl group, formyl group and myristoyl group out of the various protecting groups present at the amino terminal of peptides. Furthermore, the enzyme of the present invention sequentially releases amino acids from the amino terminal of peptides.

(2) Enzyme Activity Determination

The activity of the enzyme of the present invention is determined by the procedures described below using Met-MCA as a substrate.

a. Reaction

An enzyme preparation of which an enzyme activity is to be determined is appropriately diluted. To 5 µl of this enzyme solution, 100 µl of 20 mM PIPES-Na buffer (pH 7.6) is added, and 5 µl of 1 mM Met-MCA (dissolved in dimethyl sulfoxide) is further added thereto. After the reaction is carried out at 75° C. for 20 minutes, 10 µl of 30%-acetic acid is added to stop the reaction.

b. Measurement

The 7-amino-4-methylcoumarine produced by the reaction is quantified using Titertec Fluoroscan II (manufactured by Dainippon Pharmaceutical Co., Ltd.) at an excitation wavelength of 355 nm and a measuring wavelength of 460 nm. One unit of an enzyme is defined as the amount of an enzyme capable of producing 1 µmol of 7-amino-4-methylcoumarine per minute at a pH of 7.6 and 75° C. in the presence of Met-MCA as the substrate. The enzyme of the present invention possesses a Met-MCA decomposing activity at a pH of 7.6 and 75° C. Similarly, the enzyme of the present invention is acted on Leu-MCA, Ala-MCA, His-MCA, etc., as well as Met-MCA, to release amino acids.

(3) Substrate Specificity

Even when a protecting group is present at the amino terminal of a peptide, the enzyme of the present invention releases the protecting group from the amino terminal, and then sequentially releases each of amino acids.

The above activity can be confirmed by using a synthetic peptide of which amino terminal is blocked, as a substrate. Specifically, the activity can be confirmed by measuring the changes in the amount of amino acids released from the substrate peptide by the enzyme reaction with the passage of time, by amino acid analysis, and analyzing the peptide degradation profile. A peptide not commercially available, out of the peptides shown below, can be chemically synthesized by known methods, e.g., by the use of a peptide synthesizer, before use.

A pyroglutamyl group-releasing activity can be examined using neurotensin as a substrate. The amino acid sequence of neurotensin is shown by SEQ ID NO: 4 in Sequence Listing. Specifically, to 10 µl of 1 mM neurotensin (manufactured by Peptide Institute, Inc.) have been added 0.12 milliunits of the enzyme preparation (5 µl), 50 µl of 40 mM PIPES-Na buffer (pH 7.6), and 35 µl of distilled water to react at 37° C. for 0 to 5 hours. The reaction mixture has been assayed for free amino acids by the amino acid analysis method. As a result, a sequential release of leucine and each of subsequent amino acids from the amino terminal of neurotensin with passage of reaction time, the leucine resulting from release of pyroglutamyl group, has been confirmed, demonstrating that the enzyme of the present invention has possessed a pyroglutamyl group-releasing activity.

An acetyl group-releasing activity can be examined using α-MSH and Ac-Gly-Asp-Val-Glu-Lys as substrates. The amino acid sequences of α-MSH and Ac-Gly-Asp-Val-Glu-Lys are shown by SEQ ID NO: 5 and SEQ ID NO: 6, respectively, in Sequence Listing. Specifically, to 10 µl of 1 mM peptide substrate solution described above have been added 0.12 milliunits of the enzyme preparation (5 μl), 50 μl of 40 mM PIPES-Na buffer (pH 7.6), and 35 μl of distilled water to react at 37° C. for 0 to 5 hours. Thereafter, the reaction mixture has been assayed for free amino acids by the amino acid analysis method. As a result, it has been shown that an amino acid at the amino terminal has been first released, the amino acid resulting from release of the acetyl group, regardless of the substrate used, demonstrating that the enzyme of the present invention has possessed an acetyl group-releasing activity. Also, a sequential release of following amino acids with the passage of reaction time has been confirmed.

A formyl group-releasing activity can be examined using For-Met-Leu-Phe-Lys (manufactured by BACHEM) as a substrate. The amino acid sequence of For-Met-Leu-Phe-Lys is shown by SEQ ID NO: 7 in Sequence Listing. To 0.5 μl of 10 mM For-Met-Leu-Phe-Lys (in 30% acetic acid solution) have been added, 4 milliunits of the enzyme preparation (3.5 μl), 25 μl of 0.1 M N-ethylmorpholine, and 21 μl of distilled water to react at 37° C. for 0 to 2 hours. Thereafter, the reaction mixture has been assayed for free amino acids by the amino acid analysis method. As a result, release of methionine in the reaction mixture, the methionine resulting from release of a formyl group, has been confirmed, demonstrating that the enzyme of the present invention has possessed a formyl group-releasing activity. Also, a sequential release of subsequent amino acids with the passage of reaction time has been confirmed.

A myristoyl group-releasing activity can be examined using Myr-Phe-Ala-Arg-Lys-Gly-Ala-Leu-Arg-Gln (manufactured by BACHEM) and Myr-Gly-Ala-Gly-Ala-Ser-Ala-Glu-Glu-Lys as substrates. The amino acid sequences of Myr-Phe-Ala-Arg-Lys-Gly-Ala-Leu-Arg-Gln and Myr-Gly-Ala-Gly-Ala-Ser-Ala-Glu-Glu-Lys are shown by SEQ ID NO: 8 and SEQ ID NO: 9, respectively, in Sequence Listing. To 5 μl of 1 mM peptide substrate solution described above have been added 4 milliunits of the enzyme preparation (3.5 μl), 25 μl of 0.1 M N-ethylmorpholine acetic acid buffer (pH 9.0), and 16.5 μl of distilled water to react at 37° C. for 0 to 9 hours. Thereafter, the reaction mixture has been assayed for free amino acids by the amino acid analysis method. As a result, it has been shown that an amino acid at the amino terminal has been first released, the amino acid resulting from release of a myristoyl group, regardless of the substrate used, demonstrating that the enzyme of the present invention has possessed a myristoyl group-releasing activity. Also, a sequential release of subsequent amino acids with the passage of reaction time has been confirmed.

Also, the enzyme of the present invention possesses an aminopeptidase activity for release of amino terminal amino acids by action on the amino terminal of a peptide of which amino terminal is not blocked by a protecting group. This activity can be confirmed by the method described in *Arch. Biochem. Biophys.*, 274, pp. 241–250 (1989).

Furthermore, the enzyme of the present invention can act on the amino terminal of proteins having high-molecular weight, as well as those of short-chain polypeptides as described above. For example, this action can be confirmed using S-reduced chicken egg white lysozyme as a substrate. Specifically, to 5 μl of 1 mM S-reduced chicken egg white lysozyme (water-soluble, molecular weight about 14,000, manufactured by Wako Pure Chemical Industries) have been added 8 milliunits of the enzyme preparation (1.6 μl), 50 μl of 50 mM disodium hydrogenphosphate-sodium hydroxide buffer (pH 11.0) containing 0.1 mM $CoCl_2$, and 43.4 μl of distilled water to react at 50° C. for 0 to 240 minutes. Thereafter, the reaction mixture has been assayed for free amino acids by the amino acid analysis method. From the changes with the passage of time in the amount of amino acids produced in the reaction mixture, it has been shown that amino acids have been sequentially released from the amino terminal of the S-reduced lysozyme, demonstrating that the enzyme of the present invention also acts on the amino terminal of proteins.

(4) Optimal Temperature

As shown by FIG. 3, the optimal temperature of the enzyme preparation of the present invention is from 75° to 95° C. at a pH of 7.6. In the figure, a vertical axis shows a relative activity (%) against the maximum activity at 95° C., and a horizontal axis shows a reaction temperature (° C.).

(5) Optimal pH

As shown by FIG. 4, the optimal pH of the enzyme of the present invention is a pH in the neighborhood of 6.5 to 9.5. In the figure, a vertical axis shows a relative activity (%) when an activity at a pH of 7.2 is defined as 100; and a horizontal axis shows a pH at 75° C.

(6) Effects of Various Reagents

The activity of the enzyme of the present invention is inhibited by amastatin (manufactured by Peptide Research Institute). For example, when 0.3 milliunits of the enzyme of the present invention is treated with 5 nmol of amastatin, and the activity of the enzyme is then assayed using Met-MCA as a substrate, the enzyme activity is almost completely lost.

In addition, the activity of the enzyme of the present invention is enhanced by $CoCl_2$.

(7) Molecular Weight

The enzyme of the present invention shows a molecular weight of about 40,000 by SDS-polyacrylamide electrophoresis; and a molecular weight of about 400,000 by ultracentrifugation method.

(8) Temperature Stability

The temperature stability for the enzyme of the present invention is determined by assaying the remaining activity of the enzyme after heat treatment of the enzyme preparation at 75° C. As shown by FIG. 5, the enzyme of the present invention shows no reduction of the enzyme activity after treatment for 5 hours in 0.1 M Tris-HCl buffer (pH 8.0) containing 0.1 mM $CoCl_2$ (closed circles in the figure), and retains 80% or more of the activity when treated for 5 hours in 0.1 M Tris-HCl buffer (pH 8.0) without containing $CoCl_2$ (open circles in the figure). In the figure, a vertical axis shows a remaining activity (%) of the enzyme and a horizontal axis shows a heat treatment time (hour).

The amino terminal protecting group-releasing enzyme in the present invention includes, in addition to the enzyme mentioned above, an enzyme comprising an entire amino acid sequence as shown by SEQ ID NO: 1 in Sequence Listing, or a partial sequence thereof, the enzyme exhibiting an amino terminal protecting group-releasing activity, or a functional equivalent thereof.

The term "functional equivalent" as described in the present specification is defined as follows. A protein existing in nature can undergo mutation, such as deletion, insertion, addition and substitution, of amino acids in an amino acid sequence thereof owing to modification reaction and the like of the protein itself in vivo or during purification, besides causation such as polymorphism and mutation of the DNAs encoding it. However, it has been known that there are some proteins which exhibit substantially the same physiological activities or biological activities as a protein without mutation. Those proteins having structural differences as described above without recognizing any significant differences of the functions and the activities thereof, are referred to as "functional equivalent."

The same can be said for the resulting proteins in the case where the above mutation is artificially introduced into the amino acid sequence of a protein. In this case, more diverse mutants can be prepared. It is also known that a polypeptide resulting from substitution of a particular cysteine residue with serine in the amino acid sequence of human interleukin 2 (IL-2) retains interleukin 2 activity [*Science,* 224, 1431 (1984)]. Therefore, a polypeptide is encompassed by the scope of the present invention when the polypeptide is shown by an amino acid sequence resulting from deletion, insertion, addition or substitution of one or more amino acid residues in the amino acid sequence disclosed by the present invention (SEQ ID NO: 1 in Sequence Listing) as long as the polypeptide shows no functional differences.

In addition, it is known that some proteins have peptide regions which are not essential for activity. For example, the above peptide region includes a signal peptide at a protein secretion in extracellular or a prosequence observed in the precursor of a protease or the like. Almost these regions are removed after translation or during conversion to an active type protein. Such proteins are able to express function equivalent in the mature form, though existing in different forms in the primary structure of the immature protein.

When the protein is produced by genetic engineering, a peptide chain which is unrelated to the activity of the protein may be added at an amino terminal or at a carboxyl terminal of a desired protein. For example, in order to increase an amount of expression of the desired protein, there may be prepared a fusion protein resulting from addition of a partial portion of an amino terminal region derived from another protein expressed in high levels in a host for use to an amino terminal of the desired protein. In addition, in order to facilitate purification of the expressed protein, a peptide having an affinity for a particular substance may be added to the amino terminal or carboxyl terminal of the desired protein. When these added peptides do not give harmful affects to the activity of the desired protein, the peptide may be in the added state. In addition, as occasion demands, an appropriate treatment, such as limited cleavage by protease, may be carried out so as to be able to remove the added peptides from the desired protein.

The proteins having a peptide having a function inessential for the function of the protein, or the proteins added with the peptide, as described above, are encompassed in the scope of a "functional equivalent," as long as the proteins can express an equivalent function.

The functional equivalent of the above-mentioned amino terminal protecting group-releasing enzyme includes, for example, an enzyme resulting from at least one of deletion, insertion, addition or substitution of one or more amino acid residues in the amino acid sequence as shown by SEQ ID NO: 1 in Sequence Listing, the enzyme exhibiting an amino terminal group-releasing activity. In the present invention, embodiments of the functional equivalent are not particularly limited. Examples thereof include a modified enzyme in which an amino acid sequence is changed so as to block a N-terminal of the amino terminal protecting group-releasing enzyme of the present invention by a protecting group. For example, the above modified enzyme includes an enzyme resulting from substitution of valine of the amino acid number 2 in the amino acid sequence as shown by SEQ ID NO: 1 in Sequence Listing to aspartic acid.

The modified enzyme can be obtained by, for example, genetic engineering techniques. Specifically, the preparation of the modified enzyme can be carried out by altering the base sequence of the DNA region encoding the enzyme on the pDAP plasmid DNA by a known nucleic acid mutagenesis technique, and subsequently expressing the protein using an appropriate host. The N-terminal amino acid sequence Met-Asp of the modified enzyme has been known to function as an acetyl group addition signal sequence in a baker's yeast [*Journal of Biochemistry,* 265, pp. 19638–19643 (1990)]. It is, therefore, possible to obtain a protein of which N-terminal is acetylated, by inserting a DNA region encoding the modified enzyme into an appropriate yeast expression vector, and expressing it in an appropriate yeast host. For example, pVT103-L [*Gene,* 52, pp. 225–233 (1987)] can be used as the yeast expression vector, and BJ2168 [*FEMS Microbiology Review,* 54, pp. 17–46 (1988)] as the yeast host. In addition, by determining the amino terminal protecting group-releasing activity of the protein by the method described in the substrate specificity section above, it can be confirmed that the protein is the amino terminal protecting group-releasing enzyme of the present invention. The pVT103-L resulting from insertion of a DNA encoding an enzyme comprising an amino acid sequence as shown by SEQ ID NO: 10 in Sequence Listing, was named as pAcDAP. The yeast BJ2168 transformed with the above plasmid is named as *Saccharomyces cerevisiae* BJ2168/pAcDAP, has been deposited under accession number FERM BP-5952 with the National Institute of Bioscience and Human-Technology, Agency of Industrial Science and Technology, Ministry of International Trade and Industry, of which the address is 1–3, Higashi 1-chome, Tsukuba-shi, Ibaraki-ken, 305 Japan (date of original deposit: May 23, 1997). Even the modified enzymes described above are included in the scope of a functional equivalent as defined in the present specification, as long as they possess activity for releasing two or more amino terminal protecting groups.

The method for blocking the N-terminal of a protein with a protecting group by alteration of an amino acid sequence is not limited to this method. For example, an alternative method for acetylation [*Journal of Biological Chemistry,* 260, pp. 5382–5391 (1985)] and a method for myristoylation [*Proceedings of the National Academy of Sciences of the United States of America,* 84, pp. 2708–2712 (1987)] may be used. Furthermore, the method for blocking the N-terminal of a protein with a protecting group is not limited to methods for substitution of amino acids as those described above. For example, a chemical method [*Methods in Enzymology,* 11, pp. 565–570 (1967)] may be used.

2. DNA of Present Invention

The present invention is a DNA encoding an amino terminal protecting group-releasing enzyme of the present invention as described above. Specifically, the DNA of the present invention includes 1) a DNA encoding a polypeptide comprising an entire sequence of the amino acid sequence as shown by SEQ ID NO: 1 in Sequence Listing, or partial sequence thereof, wherein the polypeptide exhibits an amino terminal group-releasing activity; 2) a DNA comprising an entire sequence of the DNA as shown by SEQ ID NO: 2 in Sequence Listing, or a partial sequence thereof; 3) a DNA encoding the functional equivalent of the present invention; and 4) a DNA encoding a protein exhibiting an amino terminal protecting group-releasing activity, wherein the DNA is capable of hybridizing to the above 1) to 3).

The DNA of the present invention can, for example, be obtained as described below.

First, DNA 1) and 2) can be obtained from *Pyrococcus furiosus* DSM 3638, as described in the explanation for the amino terminal protecting group-releasing enzyme of the present invention.

It is also possible to obtain the DNA of a protein possessing an activity similar to that of the enzyme of the present invention, on the basis of the base sequence of the DNA encoding the amino terminal protecting group-releasing enzyme provided by the present invention. Specifically, by using the DNA encoding the enzyme of the present invention, or a portion of its base sequence, as a probe for hybridization, or a primer for a gene amplification method, such as PCR, a DNA encoding a protein possessing an activity functionally equivalent to that of the present enzyme can be screened. DNA of 3) and 4) can be obtained by the above method.

When the above method is used, a DNA fragment containing only a portion of the desired DNA is obtained in some cases. In such cases, the entire desired DNA can be obtained by examining the base sequence of the DNA fragment obtained to identify it as a portion of the desired DNA, then carrying out either hybridization to the DNA fragment or a portion thereof as a probe, or PCR using a primer synthesized on the basis of the base sequence of the DNA fragment.

The above hybridization can be carried out under the following conditions. Specifically, a DNA-immobilized membrane is incubated with a probe at 50° C. for 12 to 20 hours in 6×SSC, wherein 1×SSC indicates 0.15 M NaCl, 0.015 M sodium citrate, pH 7.0, containing 0.5% SDS, 0.1% bovine serum albumin (BSA), 0.1% polyvinyl pyrrolidone, 0.1% Ficol 400, and 0.01% denatured salmon sperm DNA. After termination of the incubation, the membrane is washed, initiating at 37° C. in 2×SSC containing 0.5% SDS, and changing the SSC concentration to 0.1×SSC from the starting level, while varying the SSC temperature to 50° C. until the signal from the immobilized DNA becomes distinguishable from the background. In addition, a novel DNA obtained as above manner can be confirmed whether the DNA is desired DNA or not, by assaying the activity possessed by a protein by means of the method as described above, the protein being encoded by the DNA.

Furthermore, it is possible to produce the above amino terminal protecting group-releasing enzyme on an industrial scale by preparing a transformant containing such DNA and then using the transformant.

It should be noted that even base sequences not identical to those disclosed in the present specification are included in the scope of the present invention, as long as they encode proteins exhibiting an amino terminal protecting group-releasing activity disclosed in the present specification as described above. The reasons therefor are as follows:

With regards to the codon (triplet base combination) determining a particular amino acid on the gene, 1 to 6 kinds are known to exist for each amino acid. Therefore, there can be a large number of DNAs encoding an amino acid sequence, though depending on the amino acid sequence. In nature, the DNA is not stable, commonly undergoing nucleic acid variation. A variation on the DNA may not affect the amino acid sequence to be encoded (silent variation); in this case, it can be said that a different DNA encoding the same amino acid sequence has been produced. The possibility is not therefore negligible that even when a DNA encoding a particular amino acid sequence is isolated, a variety of DNAs encoding the same amino acid sequence are produced with generation passage of the organism containing it. Moreover, it is not difficult to artificially produce a variety of DNAs encoding the same amino acid sequence by means of various genetic engineering techniques.

For example, when a codon used in the natural gene encoding the desired protein is low in availability in the host used to produce the protein by genetic engineering, the amount of protein expressed is sometimes insufficient. In this case, expression of the desired protein is enhanced by artificially converting the codon into another one of high availability in the host without changing the amino acid sequence encoded (for example, Japanese Examined Patent Publication No. Hei 7-102146). It is of course possible to artificially produce a variety of DNAs encoding a particular amino acid sequence, and the DNAs can be also produced in natural environment.

Furthermore, even if it is a DNA having a mutation artificially introduced to give a particular property for a protein, it is included in the scope of the DNA of the present invention, as long as it encodes the enzyme of the present invention possessing an amino terminal protecting group-releasing activity. The DNA described above includes, for instance, the DNA having the base sequence as shown by SEQ ID NO: 11 in Sequence Listing. The DNA has a base sequence resulting from substitution of the base sequence TG which is present at base numbers 5 and 6 on the base sequence as shown by SEQ ID NO: 2 in Sequence Listing, with the base sequence AT. When a protein encoded by the DNA is expressed in a yeast, an amino terminal protecting group-releasing enzyme can be obtained by substitution of amino acid number 2 valine on the amino acid sequence as shown by SEQ ID NO: 1 in Sequence Listing, with aspartic acid, and N-terminal acetylation.

3. Method for Removing Amino Terminal Protecting Group of Present Invention

The method for removing an amino terminal protecting group of the present invention is characterized in that the method comprises the step of subjecting a peptide of which amino terminal is blocked by a protecting group to a reaction with the amino terminal protecting group-releasing enzyme of the present invention or a functional equivalent thereof to release the protecting group at the amino terminal.

Specific removal methods include one in which, when an enzyme comprising the amino acid sequence as shown by SEQ ID NO: 1 in Sequence Listing is used, the protecting group can be released by reacting the enzyme with a substrate in 50 mM PIPES-Na buffer (pH 7.6) at 50° C. It should be noted, however, that as a matter of course, reaction conditions vary depending on the kind of protecting groups and peptides. It is also possible to add $CoCl_2$ to increase the activity of the enzyme.

4. Method for Analyzing Amino Acid Sequence of Present Invention

A method for analyzing an amino acid sequence of the present invention is a method for analyzing an amino acid sequence of a peptide of which amino terminal is blocked by a protecting group, characterized in that the method comprises the step of releasing the protecting group by the above removal method, and then subjecting the resulting peptide to an amino acid sequence analysis.

The method for analyzing an amino acid sequence for peptides of which amino terminal is blocked by a protecting group using the method for removing a protecting group of the present invention, includes, for example, a method comprising removing an amino terminal protecting group of a peptide to be sequenced by using the amino terminal protecting group-releasing enzyme of the present invention, and then determining the sequence from the newly produced amino terminal by the Edman degradation method.

When a sample enzymatically treated with the amino terminal protecting group-releasing enzyme of the present invention is used for analysis of an amino acid sequence by the Edman degradation method, there is the possibility that the information on the amino acid sequence of the enzyme of the present invention contaminates the information on the amino acid sequence of the sample, as detected as a noise by using an excess amount of the enzyme. In this case, use of an amino terminal protecting group-releasing enzyme having the amino acid sequence as shown by SEQ ID NO: 10 in Sequence Listing can prevent the contamination of noise by avoiding Edman degradation of the amino terminal protecting group-releasing enzyme itself. The protecting group at the N-terminal of the enzyme is not limited to the acetyl group.

In addition, when the amino terminal protecting group-releasing enzyme possesses an aminopeptidase activity, a protecting group release is followed by sequential release of amino acids by the action of the enzyme. As long as a condition under which the enzyme action can be controlled can be set, the amino acid sequence can be determined by the Edman degradation after removal of amino terminal protecting group alone, or removal of protecting group and subsequent several amino acid residues.

Furthermore, using the aminopeptidase activity described above, amino acid sequence analysis can be carried out by the methods described below. Specifically, the above methods include a method for determining a sequence by subjecting a peptide for which the sequence is to be determined to a reaction with an amino terminal protecting group-releasing enzyme, and thereafter analyzing a change with passage of time in amino acids released in the mixture; and a method for determining a sequence by identifying amino acid composition of various partially digested peptides produced in the reaction mixture, and thereafter comparing the composition. In the latter method, in particular, it is advantageous to identify the amino acid compositions of peptides by molecular weight determination based on mass spectrometric analysis. The method based on mass spectrometric analysis enables easy determination of the kinds of amino acids released based on molecular weight differences in partially digested peptides, and also enables simultaneous determination of the kind of the protecting group at the amino terminal.

5. Kit for Analysis of Amino Acid Sequence of Present Invention

A kit of the present invention for use in analyzing an amino acid sequence of a peptide of which amino terminal is blocked by a protecting group, is characterized in that the kit comprises the above enzyme of the present invention. Such kit can be used in an amino acid analysis for a peptide blocked at amino terminal by any kind of a protecting group. In addition, standards can be added to the kit, the standard using for identification of a protecting group blocking at amino terminal of a peptide.

6. Antibody, Probe and Primer of Present Invention

An antibody or a fragment thereof which specifically binds to the above amino terminal protecting group-releasing enzyme or the functional equivalent thereof can be obtained by conventional methods. Such antibody and so on is available for purification and detection of enzyme of the present invention. In addition, a synthesized oligonucleotide probe or a synthesized oligonucleotide primer, which is capable of hybridizing to the above DNA, respectively, can be obtained by conventional methods. The probe and primer is available for a detection and amplification of the DNA of present invention.

The present invention is hereinafter described by means of the following examples, but the scope of the present invention is not limited only to those examples. The % values shown in Examples below mean % by weight.

EXAMPLE 1

Preparation of Amino Terminal Protecting Group-Releasing Enzyme (1) Preparation of *Pyrococcus furiosus* Genomic DNA

*Pyrococcus furiosus* DSM3638 was cultured in the following manner:

A medium used had the following composition: 1% trypton, 0.5% yeast extract, 1% soluble starch, 3.5% Jamarin S Solid (Jamarin Laboratory), 0.5% Jamarin S Liquid (Jamarin Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_3$, 0.1 ppm $Na_2MoO_4.2H_2O$, and 0.25 ppm $NiCl_2.6H_2O$.

In a two-liter medium bottle was charged with 2 liters of the medium having the above composition, and the medium was sterilized at 120° C. for 20 minutes. Nitrogen gas was blown thereinto to remove dissolved oxygen. Next, the above strain was inoculated into the resulting medium. Thereafter, the medium was subjected to stationary culture at 95° C. for 16 hours. After the cultivation, cells were harvested by centrifugation.

The harvested cells were then suspended in 4 ml of 0.05 M Tris-HCl (pH 8.0) containing 25% sucrose. To this suspension, 0.8 ml of lysozyme [5 mg/ml, 0.25 M Tris-HCl (pH 8.0)] and 2 ml of 0.2 M EDTA (pH 8.0) were added, and the suspension incubated at 20° C. for 1 hour. After adding 24 ml of an SET solution [150 mM NaCl, 1 mM EDTA, and 20 mM Tris-HCl (pH 8.0)], 4 ml of 5% SDS and 400 μl of proteinase K (10 mg/ml) were added to the resulting mixture. Thereafter, the resulting mixture was reacted at 37° C. for 1 hour. After termination of the reaction, the reaction mixture was subjected to phenol-chloroform extraction and subsequent ethanol precipitation to prepare about 3.2 mg of genomic DNA.

(2) Preparation of Cosmid Protein Library

Four hundred micrograms of the genomic DNA from the *Pyrococcus furiosus* was partially digested with Sau3Al and fractionated by size into 35 to 50 kb DNA fractions by density gradient ultracentrifugation method. Next, one microgram of the triple helix cosmid vector (manufactured by Stratagene) was digested with BamHI. The resulting treated vector was subjected to ligation after mixing with 140 μg of the above 35 to 50 kb DNA fractions. The genomic DNA fragment from the *Pyrococcus furiosus* was packaged into lambda phage particles by in vitro packaging method using "GIGAPACK GOLD" (manufactured by Stratagene), to prepare a cosmid library.

A portion of the obtained phage solution was then transformed into *Escherichia coli* DH5αMCR to yield a cosmid clone. Several transformants out of the resulting transformants were selected to yield a cosmid. After confirmation of the presence of an insert of an appropriate size, about 500 transformants were again selected from the above library, and individually cultured in 150 ml of an LB medium (10 g/l trypton, 5 g/l yeast extract, 5 g/l NaCl, pH 7.2) containing 100 μg/ml of ampicillin. The resulting culture was centrifuged to harvest cells, and the harvested cells were suspended in 1 ml of 20 mM Tris-HCl at a pH of 8.0, and the resulting suspension was then heat-treated at 100° C. for 10 minutes. Next, ultrasonication treatment was carried out to disrupt cells, and the resulting disrupted cell suspension was heat-treated again at 100° C. for 10 minutes. The lysate obtained as a supernatant after centrifugation was used as a cosmid protein library.

(3) Selection of Cosmid Carrying Amino Terminal Protecting Group-Releasing Enzyme Gene First, a cosmid clone possessing a peptidase activity was selected out of the cosmid protein library by quantifying the amount of 7-amino-4-methylcoumarine produced with amino acid-MCAs as substrates. Specifically, 10 to 30 µl of lysates were taken from the above-described cosmid protein library, 100 µl of a 0.1 M PIPES-Na buffer (pH 7.6) and 5 µl of each of 18 kinds of 5 mM amino acid-MCAs (each dissolved in dimethyl sulfoxide) were added to the lysates to react at 90° C. for 1 to 3 hours. Thereafter, the amount of 7-amino-4-methylcoumarine produced was measured using Titertec Fluoroscan II (manufactured by Dainippon Pharmaceutical Co., Ltd.) at an excitation wavelength of 355 nm and a measuring wavelength of 460 nm. The lysates showing a decomposing activity on Met-MCA, Leu-MCA, Ala-MCA, and His-MCA were selected. Furthermore, out of these lysates, a lysate possessing an activity for sequentially releasing an acetyl group and an amino acid from the amino terminal was selected, with α-MSH as a substrate, to yield cosmid clones corresponding to the lysates.

(4) Preparation of Plasmid pDAP1 Carrying Amino Terminal Protecting Group-Releasing Enzyme Gene A cosmid was prepared from the cosmid clone obtained above possessing an activity for sequentially releasing an acetyl group and an amino acid from the amino terminal. The resulting DNA fragment after digestion of this cosmid with BamHI was inserted into a BamH site of a plasmid vector pUC18. After the resulting recombinant plasmid was introduced to *Escherichia coli* JM109, the cells were spread over an LB plate (10 g/l trypton, 5 g/l yeast extract, 5 g/l NaCl, 15 g/l agar, pH 7.2) containing 100 µg/ml of ampicillin. The transformants obtained were individually cultured in 5 ml of an LB medium containing 100 µg/ml of ampicillin. The resulting culture was centrifuged to harvest cells. The harvested cells were suspended in 50 µl of 50 mM Tris-HCl (pH 8.0), and the suspension was heat-treated at 100° C. for 10 minutes. Thereafter, the heat-treated cells were disrupted by ultrasonication treatment. The disrupted cell suspension was again heat-treated at 100° C. for 10 minutes and centrifuged, to yield a lysate. The resulting lysate was assayed for a peptidase activity.

Specifically, to 15 µl of the lysate were added 50 µl of 0.1 M PIPES-Na buffer (pH 7.6) and 5 µl of 5 mM Met-MCA (dissolved in dimethyl sulfoxide), and the mixture was reacted at 90° C. for 1.5 hours. Thereafter, the amount of 7-amino-4-methylcoumarine produced was measured using Titertec Fluoroscan II (manufactured by Dainippon Pharmaceutical Co., Ltd.) at an excitation wavelength of 355 nm and a measuring wavelength of 460 nm. A plasmid was prepared from a transformant possessing an Met-MCA decomposing activity and named as a plasmid pDAP1.

(5) Preparation of Plasmid pDAP2 Carrying Amino Terminal Protecting Group-Releasing Enzyme Gene The above plasmid pDAP1 was subjected to digestion with EcoRI, and then subjected to self-ligation. The resulting recombinant plasmid was introduced to *Escherichia coli* JM109, and then a lysate prepared from the resulting transformant by the above described method was assayed for a peptidase activity. A plasmid was prepared from the transformant, the transformant recognized to have the above enzyme activity therein, and named as a plasmid pDAP2.

(6) Preparation of Plasmid pDAP3 Carrying Amino Terminal Protecting Group-Releasing Enzyme Gene The DNA fragment of about 1.7 kb obtained by digesting the plasmid pDAP2 with SacI was inserted to a SacI site of a plasmid vector pUC18. The resulting recombinant plasmid was introduced to *Escherichia coli* JM109, and then a lysate prepared from the resulting transformant by the above described method was assayed for a peptidase activity. A plasmid was prepared from a transformant, the transformant recognized to have the above enzyme activity therein, and named as a plasmid pDAP3. A restriction endonuclease map of the plasmid pDAP3 is shown in FIG. 1.

(7) Preparation of Plasmid pDAP Carrying Amino Terminal Protecting Group-Releasing Enzyme Gene The above plasmid pDAP3 was digested with SnaBI and SacI, and the resulting digested DNA was subjected to agarose gel electrophoresis. Thereafter, a DNA fragment of about 1.2 kb was recovered from an agarose gel. The DNA fragment was inserted to a plasmid vector pUC19 using a SmaI-SacI site. The resulting recombinant plasmid was introduced to *Escherichia coli* JM109, and then a lysate prepared from the resulting transformant by the above described method was assayed for a peptidase activity. It was confirmed that the lysate further possessed an activity on α-MSH having an acetyl group at amino terminal, the activity for sequentially releasing an acetyl group and each of amino acids from amino terminal.

A plasmid was prepared from a colony recognized to have the above enzyme activity therein, and named as a plasmid pDAP. A restriction endonuclease map of the plasmid pDAP is shown in FIG. 2. The *Escherichia coli* JM109 transformed with the plasmid pDAP is named and designated as *Escherichia coli* JM109/pDAP, and has been deposited under accession number FERM BP-5804 with the National Institute of Bioscience and Human-Technology, Agency of Industrial Science and Technology, Ministry of International Trade and Industry, of which the address is 1–3, Higashi 1-chome, Tsukuba-shi, Ibaraki-ken 305 Japan (date of original deposit: Mar. 29, 1996; transfer to international deposit: Jan. 30, 1997).

(8) Determination of Base Sequence of Amino Terminal Protecting Group-Releasing Enzyme Gene The DNA fragment of about 1.2 kb containing the above-described amino terminal protecting group-releasing enzyme gene inserted to the plasmid pDAP was digested with various restriction endonucleases to fragmentate to an appropriate size. Each fragment was inserted into a plasmid vector to determine a base sequence. The base sequencing of each inserted fragment was carried out by a dideoxy method using the BcaBEST dideoxy sequencing kit (manufactured by Takara Shuzo Co., Ltd.), and the obtained data of each fragment was compared and put in order, to determine an entire base sequence of the DNA fragment of 1.2 kb.

The base sequence of the DNA fragment of about 1.2 kb is shown by SEQ ID NO:3 in Sequence Listing, the fragment containing DNA encoding the amino terminal protecting group-releasing enzyme inserted in the plasmid pDAP. In the sequence, base numbers 86 through 88 represent the initiation codon, base numbers 1130 through 1132 represent the termination codon, and an open reading frame therebetween was deduced to be the structural gene region of the enzyme.

The base sequence of the above-described open reading frame is shown by SEQ ID NO:2 in Sequence Listing. The amino acid sequence of the amino terminal protecting group-releasing enzyme of the present invention is shown by SEQ ID NO:1 in Sequence Listing, the amino acid sequence being deduced from the base sequence shown by SEQ ID NO:2.

(9) Preparation of Enzyme Preparation

*Escherichia coli* JM109/pDAP was inoculated into 12 test tubes each containing 5 ml of an LB medium supplemented with 100 μg/ml of ampicillin, and cultured at 37° C., under conventional cultivation conditions. When the culture broth turbidity reached $A_{660}$ of 1, isopropyl-β-D-thiogalactopyranoside was added so as to have a final concentration of 1 mM, followed by further cultivation at 37° C. for 16 to 18 hours.

A total of 60 ml of the culture broth obtained above was centrifuged to harvest cells. The cells obtained were suspended in 0.6 ml of buffer A (20 mM Tris-HCl, pH 8.0) and heat-treated at 100° C. for 10 minutes, and the heat-treated cells were then disrupted by ultrasonication treatment. The cells were again heat-treated at 100° C. for 10 minutes and centrifuged to yield a lysate. The lysate obtained was subjected to gel filtration through 50 ml of Sephacryl S-300 HR (manufactured by Pharmacia) column, the column being previously equilibrated with buffer B (50 mM Tris-HCl, pH 8.0), and a fraction with an Met-MCA decomposing activity was collected. Further, this active fraction was then adsorbed to 5 ml of Econopac highQ cartridge (manufactured by Bio-Rad) column, the column being previously equilibrated with the buffer B. The adsorbed column was washed with the buffer B, and eluted by a linear density gradient of 0 to 0.5 M NaCl. The eluate was assayed for the Met-MCA decomposing activity, and the resulting active fraction was collected to yield a purified enzyme preparation.

One unit of the purified enzyme preparation obtained was defined as the amount of enzyme capable of producing 1 μmol of 7-amino-4-methylcoumarine in one minute at a pH of 7.6 and 75° C. when using the Met-MCA as the substrate.

EXAMPLE 2

Physicochemical Properties of Enzyme Preparation Prepared in Example 1

1) Optimal Temperature

The determination of optimal temperature was carried out by the following procedures: Specifically, an enzyme activity was determined at various temperatures by a method for determining an enzyme activity with Met-MCA as a substrate using 18 microunits of the enzyme preparation. As shown in FIG. 3, the enzyme of the present invention possessed activity in the temperature range from 25° to 95° C. at a pH of 7.6, showing the highest activity at the maximum temperature measured of 95° C. As shown in FIG. 3, the optimal temperature for the enzyme preparation of the present invention ranged from 75° to 95° C. at a pH of 7.6. In the figure, the vertical axis indicates relative activity (%) to the maximum activity (95° C.), and the horizontal axis indicates reaction temperature (° C.).

2) Optimal pH

The determination of optimal pH was carried out by the following procedures: Specifically, an enzyme activity was determined by one of the above-described method for determining an enzyme activity with an Met-MCA as a substrate using 18 microunits of the enzyme preparation, in which the pH of the buffer added to the reaction mixture was made variable. As shown in FIG. 4, the optimal pH for the enzyme of the present invention was in the range from about a pH of 6.5 to a pH of 9.5. In the figure, the vertical axis indicates relative activity (%) to the activity at a pH of 7.2 as 100, and the horizontal axis indicates pH at 75° C. As to buffers used for a determination of an activity, there were used 20 mM sodium acetate buffers at a pH of 4.1 to a pH of 5.1; 20 mM PIPES-Na buffers at a pH of 5.8 to a pH of 7.2; 20 mM sodium borate buffers at a pH of 8.0 to a pH of 9.5; and 20 mM disodium hydrogenphosphate-sodium hydroxide buffers at a pH of 9.9 to a pH of 10.6. These pH values were obtained at 75° C.

3) Affects of Various Reagents

The activity of the enzyme of the present invention was inhibited by amastatin. For example, when 3 milliunits of the enzyme of the present invention was treated at 37° C. for 30 minutes in 50 μl of 20 mM borate buffer (pH 10.0) containing 1 mM of amastatin, and a 5 μl portion was then assayed for activity by the method of determining an enzyme activity in item (2) above, the activity found was 1.5% of that obtained when the enzyme was treated with an amastatin-free buffer.

Also, the activity of the enzyme of the present invention was enhanced by $CoCl_2$. For example, when $CoCl_2$ was added so as to have a final concentration of 91 μM to the above-described assay system using an Met-MCA, the activity found was about 6 times that without such addition.

4) Molecular Weight

The molecular weight of the enzyme of the present invention was about 40,000 as determined by SDS-polyacrylamide electrophoresis and about 400,000 as determined by ultracentrifugation method.

5) Temperature Stability

The remaining activity of the enzyme preparation after heat treatment was examined to evaluate the temperature stability of the enzyme of the present invention. Specifically, a 0.1 M Tris-HCl buffer (pH 8.0) containing 26 milliunits of the enzyme preparation, or a buffer containing enzyme with $CoCl_2$ added so as to make a final concentration of 0.1 mM, was treated at 75° C. for 0 to 5 hours. Thereafter, a portion of the treated mixture was assayed for the remaining activity of the enzyme. Here, the determination of an activity was carried out by means of a method for determining an enzyme activity by the above-described system using an Met-MCA as a substrate.

As shown in FIG. 5, the enzyme of the present invention showed no reduction in an enzyme activity even after a treatment for 5 hours in a 0.1 M Tris-HCl buffer (pH 8.0) containing 0.1 mM $CoCl_2$. The enzyme also retained 80% or more activity even after a treatment for 5 hours in a buffer without containing $COCl_2$. In the figure, the vertical axis indicates the remaining activity of the enzyme (%), and the horizontal axis indicates time for heat treatment (hours).

EXAMPLE 3

Confirmation of Amino Terminal Protecting Group-Releasing Activity of Enzyme Preparation Prepared in Example 1

The actions of the enzyme of the present invention on synthetic peptides with a blocked amino terminal were evaluated using the enzyme preparation prepared in Example 1.

(1) Action on Pyroglutamyl Group

To 10 μl of 1 mM neurotensin were added 0.12 milliunits of the enzyme preparation (5 μl), 50 μl of 40 mM PIPES-Na buffer (pH 7.6), and 35 μl of distilled water to react at 37° C. for 0, 1, 3, or 5 hours. A portion of the reaction mixture was taken and subjected to amino acid analysis using the L-8500 high speed amino acid analyzer (manufactured by Hitachi Ltd.) to quantify free amino acids produced in the reaction mixture. The results are shown in FIG. 6. As shown in FIG. 6, leucine, tyrosine, and glutamic acid, all present on the amino-terminal side of neurotensin, were released in the reaction mixture. The changes with the passage of time in their amounts produced demonstrated that the enzyme of the present invention acted on neurotensin from the amino terminal side to sequentially release each of amino acids. Also, since leucine was detected as a free amino acid, it was clearly demonstrated that the enzyme of the present invention cleaved the bond between the pyroglutamyl group and leucine.

(2) Action on Acetyl Group

To 1 mM α-MSH (10 μl) were added 0.12 milliunits of the enzyme preparation (5 μl), 50 μl of 40 mM PIPES-Na buffer (pH 7.6), and 35 μl of distilled water to react at 37° C. for 0, 1, 3, or 5 hours. Thereafter, free amino acids resulting from the reaction were analyzed in the same manner as above. The results are shown in FIG. 7. As shown in FIG. 7, the amount of amino acid released from α-MSH increased as the position of the amino acid was closer to the amino terminal (serine was detected in more amounts than other amino acids, because it was present at two positions, i.e., amino terminal and third position from the amino terminal), demonstrating that the enzyme of the present invention acts on α-MSH from the amino-terminal side, and that the enzyme cleaved the bond between the acetyl group and serine.

In addition, the results of an experiment carried out in the same manner as the case of α-MSH, except that the substrate was replaced with Ac-Gly-Asp-Val-Glu-Lys (SEQ ID NO:6), are shown in FIG. 8. As shown in FIG. 8, glycine was released in the reaction mixture, suggesting that the enzyme of the present invention sequentially cleaved the bond between the acetyl group and glycine, and then the glycine-aspartic acid bond. In the reaction mixture, trace amounts of aspartic acid and valine were detected, as well as glycine.

(3) Action on Formyl Group

To 0.5 μl of 10 mM For-Met-Leu-Phe-Lys (SEQ ID NO:7) (in 30% acetic acid solution) were added 4 milliunits of the enzyme preparation (3.5 μl), 25 μl of 0.1 M N-ethylmorpholine, and 21 μl of distilled water to react at 37° C. for 0, 20, 40, 60, or 120 minutes. Thereafter, free amino acids resulting from the reaction were analyzed in the same manner as above. The results are shown in FIG. 9. As shown in FIG. 9, methionine resulting from release of a formyl group was first released in the reaction mixture, demonstrating that the enzyme of the present invention possessed a formyl group-releasing activity. The changes with the passage of time in the production of other amino acids (leucine, phenylalanine, lysine) demonstrated that the enzyme sequentially released each of amino acids from the amino-terminal side of the above-described substrate peptide.

(4) Action on Myristoyl Group

Figure 10:
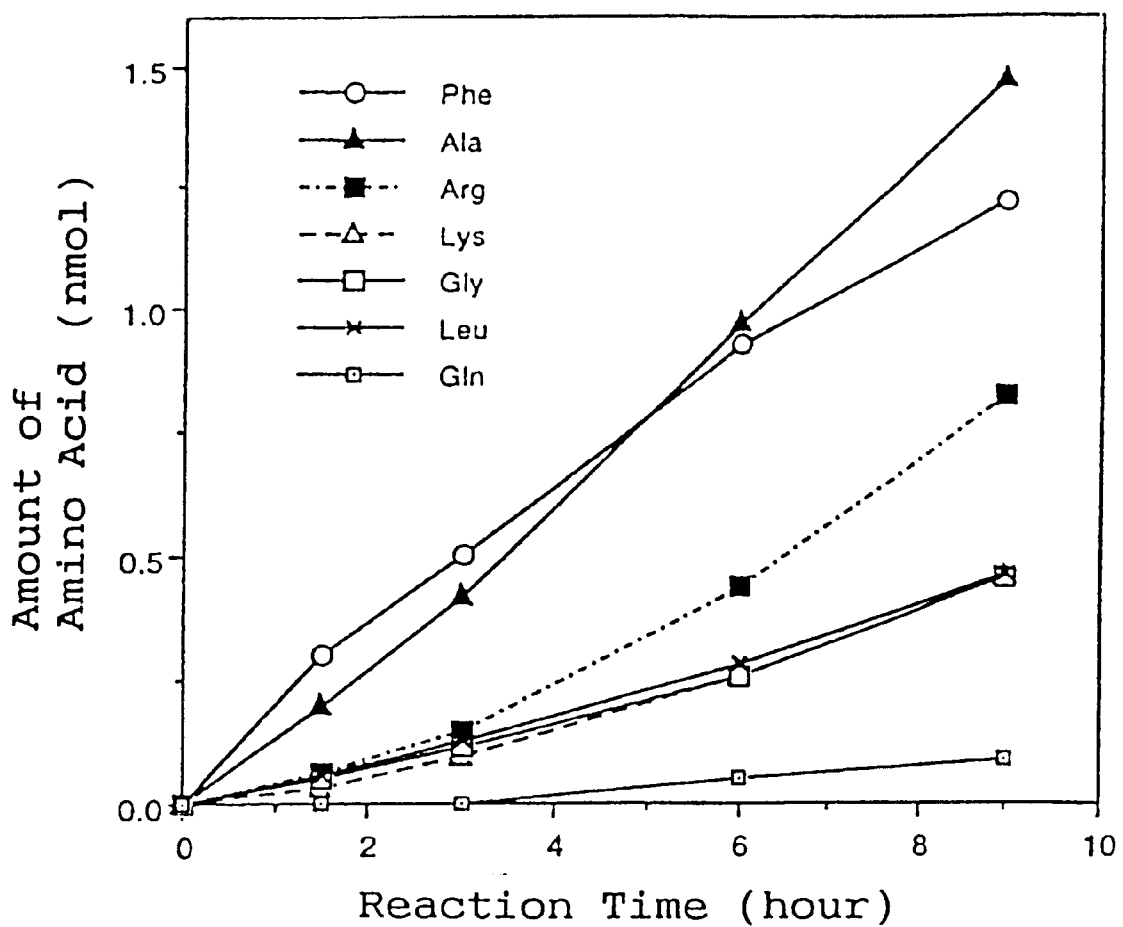
FIG. 10 is a graph showing an action of an amino terminal protecting group-releasing enzyme in the present invention with the passage of time on Myr-Phe-Ala-Arg-Lys-Gly-Ala-Leu-Arg-Gln (SEQ ID NO:8).

To 5 μl of 1 mM solution of Myr-Phe-Ala-Arg-Lys-Gly-Ala-Leu-Arg-Gln (SEQ ID NO:8) were added 4 milliunits of the enzyme preparation (3.5 μl), 25 μl of 0.1 M N-ethylmorpholine acetic acid buffer (pH 9.0), and 16.5 μl of distilled water to react 37° C. for 0, 1.5, 3, 6, or 9 hours. Thereafter, free amino acids resulting from the reaction were analyzed in the same manner as above. The results are shown in FIG. 10. As shown in FIG. 10, a phenylalanine resulting from release a myristoyl group was first released in the reaction mixture, demonstrating that the enzyme of the present invention possessed a myristoyl group-releasing activity. The changes with the passage of time in the production of other amino acids demonstrated that the enzyme sequentially released each of amino acids from the amino-terminal side of the above-described substrate peptide.

The results of an experiment carried out in the same manner as above, except that the substrate was replaced with Myr-Gly-Ala-Gly-Ala-Ser-Ala-Glu-Glu-Lys (SEQ ID NO:9), are shown in FIG. 11. It is difficult to determine the order of amino acids released from the results shown in FIG. 11, because the above-described substrate peptide has 2 residues of glycine and 3 residues of alanine in the molecule. The results suggested that the enzyme of the present invention acted on the substrate from the amino-terminal side, and that the enzyme of the present invention possessed a myristoyl group-releasing activity.

EXAMPLE 4

Confirmation of Aminopeptidase Activity of Enzyme Preparation Prepared in Example 1 for Protein The action of the above-described enzyme preparation on a protein was evaluated with an S-reduced chicken egg white lysozyme as a substrate.

To 5 μl of a 1 mM S-reduced chicken egg white lysozyme (water-soluble, molecular weight about 14,000, manufactured by Wako Pure Chemical Industries) were added 8 milliunits of the enzyme preparation (1.6 μl), 50 μl of a 50 mM disodium hydrogenphosphate-sodium hydroxide buffer (pH 11.0) containing 0.1 mM $CoCl_2$, and 43.4 μl of distilled water to react at 50° C. for 0, 40, 80, 120, 180, or 240 minutes. A portion of the reaction mixture was taken and subjected to amino acid analysis using L-8500 high speed amino acid analyzer (manufactured by Hitachi Ltd.) to quantify free amino acids produced in the reaction mixture. The results are shown in FIG. 12. As shown in FIG. 12, lysine, valine, phenylalanine, glycine, and arginine, all present at the amino terminal of the S-reduced lysozyme, were released in the reaction mixture. The changes with the passage of time in their amounts produced demonstrated that the enzyme of the present invention acted on the reduced lysozyme from the amino-terminal side and amino acids were sequentially released.

Here, the amino acid sequence of the S-reduced lysozyme used was Lys-Val-Phe-Gly-Arg (SEQ ID NO:17) . . . , as indicated from the amino terminal.

EXAMPLE 5

Preparation of Amino Terminal Protecting Group-Releasing Enzyme of Which N-Terminal Is Blocked by Acetyl Group (1) Modification of Amino Terminal Protecting Group-Releasing Enzyme Gene A mutation was introduced to pDAP to change the N-terminal amino acid sequence of an enzyme comprising the amino acid sequence as shown by SEQ ID NO:1 in Sequence Listing to the acetyl group addition signal Met-Asp. Specifically, PCR was carried out with pDAP DNA as a template, using a synthetic DNA comprising the base sequence as shown by SEQ ID NO:12 in Sequence Listing for replacement of the codon for valine as the second amino acid as numbered from the N-terminal of the enzyme with the codon for aspartic acid, and another synthetic DNA comprising the base sequence as shown by SEQ ID NO:13 for destruction of the HindIII and SphI restriction endonuclease sites on a sequence within the multicloning site on the plasmid pDAP, as a pair of primers. After completion of the PCR, the resulting reaction mixture was enzymatically treated with SphI (manufactured by Takara Shuzo Co., Ltd.) to digest the plasmid without the mutation. Thereafter, the digested plasmid was introduced to *Escherichia coli* JM109 (manufactured by Takara Shuzo Co., Ltd.), and the desired mutated plasmid was prepared from the transformant obtained. Next, PCR was carried out with this plasmid DNA as a template, using a synthetic DNA comprising the base sequence as shown by SEQ ID NO:14 in Sequence Listing for introduction of a BamHI site immediately upstream of the initiation codon for protein in the coding region for a protein on the DNA, and another synthetic DNA comprising a complementary base sequence in the downstream region of the coding region for a protein on the DNA, as shown by SEQ ID NO:15 in Sequence Listing, as a pair of primers. The reaction mixture was subjected to agarose electrophoresis, and the resulting DNA fragment of about 1.2 kb amplified was recovered from the agarose gel. This DNA fragment was digested with BamHI (manufactured by Takara Shuzo Co., Ltd.) and HindIII (manufactured by Takara Shuzo Co., Ltd.), and inserted into the BamHI and HindIII sites of the plasmid vector pVT103-L, an *Escherichia coli*-yeast shuttle vector. This recombinant plasmid was introduced to *Escherichia coli* JM109, and a plasmid DNA was prepared from the transformant obtained.

(2) Expression of Modified Enzyme

After the plasmid DNA obtained was introduced to the yeast BJ2168, transformants obtained on an auxotrophic plate (6.7 g/l yeast nitrogen base, 20 g/l glucose, 20 mg/l tryptophan, 20 mg/l histidine, 20 mg/l uracil, 15 g/l agar) were each inoculated into a test tube containing 5 ml of YPD medium (10 g/l yeast extract, 20 g/l peptone, 20 g/l glucose) and cultured at 30° C. for 16 hours. Each culture broth was transferred to a conical flask containing 500 ml of the above-described auxotrophic medium and cultured at 30° C. for 16 hours. The culture broth was centrifuged to harvest cells. The cells obtained were suspended in 50 ml of buffer C (1 M sorbitol, 50 mM Tris-HCl, pH 7.5, 30 mM DTT) and incubated at 30° C. for 10 minutes, followed by centrifugation. The cells obtained were further suspended in 10 ml of buffer D (1 M sorbitol, 50 mM Tris-HCl, pH 7.5, 2 mM DTT), and Zymolyase-100T (manufactured by Seikagaku Corp.) was added so as to a final concentration of 0.5 mg/ml, followed by incubation at 30° C. for 30 minutes and subsequent centrifugation, to yield a protoplast. The protoplast obtained was then suspended in 20 ml of buffer E (50 mM Tris-HCl, pH 7.5, 2 mM DTT). EDTA, KCl, and Triton X-100 were added so as to respective final concentrations of 1 mM, 0.2 M, and 0.2%, followed by incubation at 37° C. for 5 minutes. This suspension was heat-treated at 100° C. for 15 minutes, and then centrifuged to yield a lysate. From this lysate, a modified enzyme preparation was prepared, by the same purification method as that for amino terminal protecting group-releasing enzyme described in item (9) of Example 1. One unit of the modified enzyme preparation was defined as the amount of enzyme capable of producing 1 $\mu$mol of 7-amino-4-methylcoumarine in one minute at a pH of 7.6 and 75° C. in the presence of an Met-MCA as the substrate. The yeast expressing the above protein is named and designated as *Saccharomyces cerevisiae* BJ2168/pAcDAP, and has been deposited under accession number FERM BP-5952 with the National Institute of Bioscience and Human-Technology, Agency of Industrial Science and Technology, Ministry of International Trade and Industry, of which the address is 1–3, Higashi 1-chome, Tsukuba-shi, Ibaraki-ken, 305 Japan (date of original deposit: May 23, 1997).

(3) Determination of Amino Terminal Protecting Group-Releasing Activity of Modified Enzyme The amino terminal protecting group-releasing activity of the modified enzyme preparation prepared in item (2) was determined by the methods as described in items (2) and (4) of Example 3. As a result, the modified enzyme exhibited a releasing activity on acetyl group and myristoyl group at N-terminal of the peptide. In addition, the modified enzyme exhibited an activity for sequentially releasing each of amino acids from N-terminal of the peptide.

(4) Confirmation of N-terminal Acetylation of Modified Enzyme

It was confirmed by mass spectrometric analysis whether the N-terminal of the modified enzyme was acetylated. Specifically, the mass of the enzyme prepared in Example 1 and that of the modified enzyme were determined, using API/300 (manufactured by PE-Sciex), and the difference of mass was calculated. As a result, the molecular weight of the enzyme prepared in Example 1 and expressed in *Escherichia coli* was determined as 38,586, and that of the modified enzyme as 38,643. The difference of molecular weight of 57 between the two enzymes was identical to the sum of the difference of molecular weight of 15 owing to valine replacement with asparagine, and the increment of molecular weight of 42 owing to acetyl group addition.

The modified enzyme was further applied to the HP G1000A protein sequencer (manufactured by Hewlett Packard) employing a method for analyzing an N-terminal amino acid sequence based on Edman degradation. However, no signal was obtained, demonstrating that the modified enzyme did not undergo Edman degradation.

(5) Peptide Amino Terminal Sequence Analysis Using Modified Enzyme

A carboxymethylated product of N-terminal acetylated bovine erythrocyte superoxide dismutase (molecular weight of 15,551, manufactured by Warthington Biochemical Corporation) was used as a substrate for the modified enzyme. To 5 $\mu$l of a 0.4 mM solution of the substrate were added 600 milliunits of the modified enzyme standard prepared in item (2) above (52 $\mu$l), 100 $\mu$l of 100 mM trimethylamine-HCl buffer (pH 11.0), 2 $\mu$l of 10 mM $CoCl_2$, and 41 $\mu$l of distilled water to react at 50° C. for 48 hours. The resulting reaction mixture was directly applied to the HP G1000A protein sequencer for an amino acid sequence analysis. The amino acid sequence data obtained are shown by SEQ ID NO:16 in Sequence Listing. This sequence was identical to the known amino acid sequence of the superoxide dismutase used as the substrate. In the amino acid sequence analysis, there was no contamination of a signal other than the amino acid sequence of the above-described superoxide dismutase.

EXAMPLE 6

Analysis of Amino Terminal Sequence of Peptide by Mass Spectrometric Analysis

The enzyme preparation prepared in Example 1 in combination with For-Met-Leu-Phe-Lys as a substrate use to carry out an amino-terminal sequence analysis of a peptide using mass spectrometric analysis.

To 1.5 $\mu$l of 10 mM For-Met-Leu-Phe-Lys (SEQ ID NO:7) (30% acetic acid solution) were added 2.4 milliunits of enzyme preparation (2.1 $\mu$l), 75 $\mu$l of 0.1 M ammonium hydrogencarbonate, 1 MM $CoCl_2$ (15 $\mu$l), and 56.4 $\mu$l of distilled water to react at 30° C. for 4 hours. Thereafter, 15 $\mu$l of formic acid was added to stop the reaction. Next, the resulting reaction mixture was then subjected to a reversed-phase HPLC (high-performance liquid chromatography) using the DEVELOSIL ODS-HG-5 column (manufactured by NOMURA CHEMICAL), and four peptide-containing peaks were collected from the reaction mixture. The molecular weight of the peptide contained in each peak was determined using the JMS-HX100 double-convergence FAB mass spectrometer (manufactured by JEOL). The elution time for individual peaks, the molecular weights of the peaks contained in the peaks, and the sequences of respective peptides deduced from these molecular weights are shown in Table 1.

TABLE 1

| Peak Number | Elution Time (minute) | Found Molecular Weight | Deduced Sequence |
|---|---|---|---|
| 1 | 12.125 | Not Determined | — |
| 2 | 21.008 | 407.3 | Leu-Phe-Lys |
| 3 | 27.358 | 538.3 | Met-Leu-Phe-Lys |
| 4 | 32.583 | 566.4 | For-Met-Leu-Phe-Lys |

As shown in Table 1, a peptide separated as peak 4 of the peptides produced in the reaction mixture was found to be the unreacted substrate peptide. The molecular weight of the peptide contained in peak 3 was identical to the molecular weight of a peptide resulting from a formyl group release from the substrate peptide. Further, the molecular weight of the peptide contained in peak 2 agreed with the molecular weight of a peptide resulting from formyl group and methionine release from the substrate peptide. These results have clarified that the enzyme of the present invention acts on the substrate peptide from the amino terminal side and a formyl group and methionine are sequentially released. It was also demonstrated that the amino terminal sequences of peptides, including the kind of the protecting group at the amino terminal, could be determined by accurately determining the molecular weights of various partially degraded peptides obtained by reacting the enzyme of the present invention on the peptides, and comparing them.

INDUSTRIAL APPLICABILITY

The amino terminal protecting group-releasing enzyme of the present invention exhibits an amino terminal protecting group releasing activity on two or more kinds of protecting groups. In addition, according to the present invention, there is provided a method for removing an amino terminal protecting group of a peptide using the enzyme. The enzyme is useful for an analysis of an amino acid sequence of a peptide, particularly a protein or peptide of which amino terminal is blocked by unconfirmed protecting groups. The present invention also provides a DNA encoding the enzyme, and a method for producing the above enzyme. An N-terminal acetylated amino terminal protecting group releasing enzyme, the enzyme prepared by altering the DNA, is useful, since the enzyme does not undergo Edman degradation, so that particularly in the method for analysis of the amino acid sequence using Edman degradation, information of the amino acid sequence derived from the enzyme does not result in noise.

What is claimed is:

1. A purified amino terminal protecting group-releasing enzyme from Pyrococcus characterized in that said enzyme possesses an activity for releasing a protecting group by acting on a peptide of which amino terminal is blocked by the protecting group (hereinafter abbreviated as a term "amino terminal protecting group-releasing activity"), and exhibits said activity for two or more protecting groups selected from the group consisting of acetyl group, pyroglutamyl group, formyl group and myristoyl group, wherein the enzyme possesses the following physicochemical properties:

(1) optimal temperature: 75° to 95° C. at a pH of 7.6;
(2) optimal pH: a pH of 6.5 to 9.5; and
(3) effects of various reagents: the activity being inhibited by amastatin and enhanced by $CoCl_2$.

2. The enzyme according to claim 1, wherein the enzyme further possesses an amino peptidase activity.

3. A purified amino terminal protecting group-releasing enzyme comprising an entire sequence of the amino acid sequence as shown by SEQ ID NO: 1 in Sequence Listing, or a partial sequence thereof, wherein said enzyme possesses an amino terminal protecting group-releasing activity, and exhibits said activity for at least two protecting groups.

4. A purified amino terminal protecting group-releasing enzyme comprising an entire sequence of the amino acid sequence as shown by SEQ ID NO: 10 in Sequence Listing, or a partial sequence thereof, wherein said enzyme possesses an amino terminal protecting group-releasing activity, and exhibits said activity for at least two protecting groups.

5. A DNA encoding a polypeptide comprising an entire sequence of the amino acid sequence as shown by SEQ ID NO:1 in Sequence Listing, or a partial sequence thereof, wherein said polypeptide exhibits an amino terminal protecting group-releasing activity.

6. The DNA according to claim 5, encoding a polypeptide exhibiting an amino terminal protecting group-releasing activity, wherein said DNA comprises an entire sequence of the DNA as shown by SEQ ID NO: 2 in Sequence Listing, or a partial sequence thereof.

7. A DNA hybridizing to a DNA encoding a polypeptide comprising an entire sequence of the amino acid sequence as shown by SEQ ID NO: 1, or an enzymatically active partial sequence thereof, wherein said DNA which hybridizes encodes a polypeptide which exhibits an amino terminal protecting group-releasing activity, said activity for two or more protecting groups, wherein hybridization is carried out under the following conditions:

wherein a DNA-immobilized membrane is incubated with a probe at 50° C. for 12 to 20 hours in 6×SSC, wherein 1×SSC indicates 0.15 M NaCl, 0.015 M sodium citrate, pH 7.0, containing 0.5% SDS 0.1% bovine serum albumin (BSA), 0.1% polyvinyl pyrrolidone, 0.1% Ficol 400, and 0.01% denatured salmon sperm DNA.

8. The DNA according to claim 7, wherein said DNA has the base sequence as shown by SEQ ID NO:11 in Sequence Listing.

9. A recombinant DNA comprising the DNA according to claim 5, 6, 8, 7.

10. An expression vector for a microorganism, an animal cell or a plant cell as a host cell, wherein the recombinant DNA according to claim 9 is inserted in said expression vector.

11. A transformant which is transformed with the expression vector according to claim 10.

12. A method for producing an amino terminal protecting group-releasing enzyme comprising the steps of culturing the transformant according to claim 11, and collecting from a culture a protein possessing an amino terminal protecting group-releasing activity or a polypeptide possessing an activity functionally equivalent to that of the protein.

13. The enzyme according to claim 3, wherein the enzyme exhibits an amino terminal protecting group-releasing activity for two or more protecting groups selected from the group consisting of acetyl group, pyroglutamyl group, formyl group and myristoyl group.

14. The enzyme according to claim 3, wherein the enzyme further possesses an amino peptidase activity.

15. The enzyme according to claim 3, wherein said enzyme possesses the following physicochemical properties:

(1) optimal temperature: 75° to 95° C. at a pH of 7.6;
(2) optimal pH: a pH of 6.5 to 9.5; and
(3) effects of various reagents: the activity being inhibited by amastatin and enhanced by $CoCl_2$.

16. An amino terminal protecting group-releasing enzyme encoded by DNA according to any one of claims 5, 6, 8 or 7.

17. A method for removing an amino terminal protecting group, comprising the steps of subjecting a peptide of which amino terminal is blocked by a protecting group to a reaction with the amino terminal protecting group-releasing enzyme according to any one of claims 1, 2, 3, 13, 14, 15, or 16 to release the protecting group at the amino terminal.

18. A method for analyzing an amino acid sequence of a peptide of which amino terminal is blocked by a protecting group, comprising the steps of releasing the protecting group by the method for removing according to claim 17, and then subjecting the resulting peptide to an amino acid sequence analysis.

19. A kit for use in analyzing an amino acid sequence of a peptide of which amino terminal is blocked by a protecting group, characterized in that the kit comprises the amino terminal protecting group-releasing enzyme according to any one of claims 1, 2, 3, 13, 14, 15 or 16.

* * * * *